United States Patent
Akagane

(10) Patent No.: US 10,426,978 B2
(45) Date of Patent: Oct. 1, 2019

(54) ULTRASONIC TREATMENT APPARATUS

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/013,486

(22) Filed: Feb. 2, 2016

(65) Prior Publication Data

US 2016/0144204 A1 May 26, 2016

Related U.S. Application Data

(63) Continuation of application No. PCT/JP2014/070869, filed on Aug. 7, 2014.

(60) Provisional application No. 61/863,104, filed on Aug. 7, 2013.

(51) Int. Cl.
| | |
|---|---|
| *A61N 7/00* | (2006.01) |
| *A61B 18/14* | (2006.01) |
| *A61B 18/00* | (2006.01) |
| *A61B 17/32* | (2006.01) |

(52) U.S. Cl.
CPC .......... *A61N 7/00* (2013.01); *A61B 18/1445* (2013.01); *A61B 17/320092* (2013.01); *A61B 2018/00101* (2013.01); *A61B 2018/00136* (2013.01); *A61B 2018/00589* (2013.01); *A61B 2018/00607* (2013.01); *A61B 2018/1452* (2013.01)

(58) Field of Classification Search
CPC .......................................... A61B 2018/00607
See application file for complete search history.

(56) References Cited

U.S. PATENT DOCUMENTS

| | | | |
|---|---|---|---|
| 6,221,069 B1 | 4/2001 | Daikuzono | |
| 2001/0003798 A1* | 6/2001 | McGovern | A61B 18/1485 606/41 |

(Continued)

FOREIGN PATENT DOCUMENTS

| | | |
|---|---|---|
| EP | 2589347 A1 | 5/2013 |
| JP | H10-211209 A | 8/1998 |

(Continued)

OTHER PUBLICATIONS

Sep. 1, 2015 Office Action issued in Japanese Patent Application No. 2015-509247.

(Continued)

*Primary Examiner* — Luther Behringer
(74) *Attorney, Agent, or Firm* — Oliff PLC

(57) ABSTRACT

An ultrasonic treatment apparatus includes a probe main body performing a vibration including a longitudinal vibration in a vibrating direction parallel to a longitudinal axis, and a distal treatment section positioned on a distal direction side with respect to a most distal node position positioned most distally among node positions of the longitudinal vibration in the probe main body. A probe side facing surface is provided in a position facing a jaw in a surface of the distal treatment section. A coating portion is made of a material having a higher heat resistance than the probe main body, and coats a surface facing a side opposite to the probe side facing surface in the probe main body.

22 Claims, 12 Drawing Sheets

(56) References Cited

U.S. PATENT DOCUMENTS

| | | | |
|---|---|---|---|
| 2005/0004560 A1* | 1/2005 | Cox | A61L 29/085 606/1 |
| 2008/0023710 A1 | 1/2008 | Park et al. | |
| 2008/0171938 A1* | 7/2008 | Masuda | A61B 17/320092 600/437 |
| 2008/0234710 A1* | 9/2008 | Neurohr | A61B 17/320068 606/169 |
| 2009/0143806 A1 | 6/2009 | Witt et al. | |
| 2011/0196399 A1 | 8/2011 | Robertson et al. | |
| 2012/0101493 A1* | 4/2012 | Masuda | A61B 17/320092 606/34 |
| 2012/0277778 A1 | 11/2012 | Masuda et al. | |
| 2014/0135804 A1* | 5/2014 | Weisenburgh, II | A61B 17/320092 606/169 |

FOREIGN PATENT DOCUMENTS

| | | |
|---|---|---|
| JP | H11-347041 A | 12/1999 |
| JP | 2001-346806 A | 12/2001 |
| JP | 3310532 B2 | 8/2002 |
| JP | 2010-522034 A | 7/2010 |
| JP | 2011-505198 A | 2/2011 |
| JP | 2013-519437 A | 5/2013 |
| JP | 2014-506148 A | 3/2014 |
| WO | 2011/099571 A1 | 8/2011 |
| WO | 2012/079025 A1 | 6/2012 |

OTHER PUBLICATIONS

Oct. 28, 2014 Search Report issued in International Patent Application No. PCT/JP2014/070869.
Feb. 18, 2016 IPRP issued in International Patent Application No. PCT/JP2014/070869.
Mar. 1, 2017 Extended European Search Report issued in European Patent Application No. 14834274.4.
May 31, 2017 Office Action issued in Chinese Patent Application No. 201480044291.2.

* cited by examiner

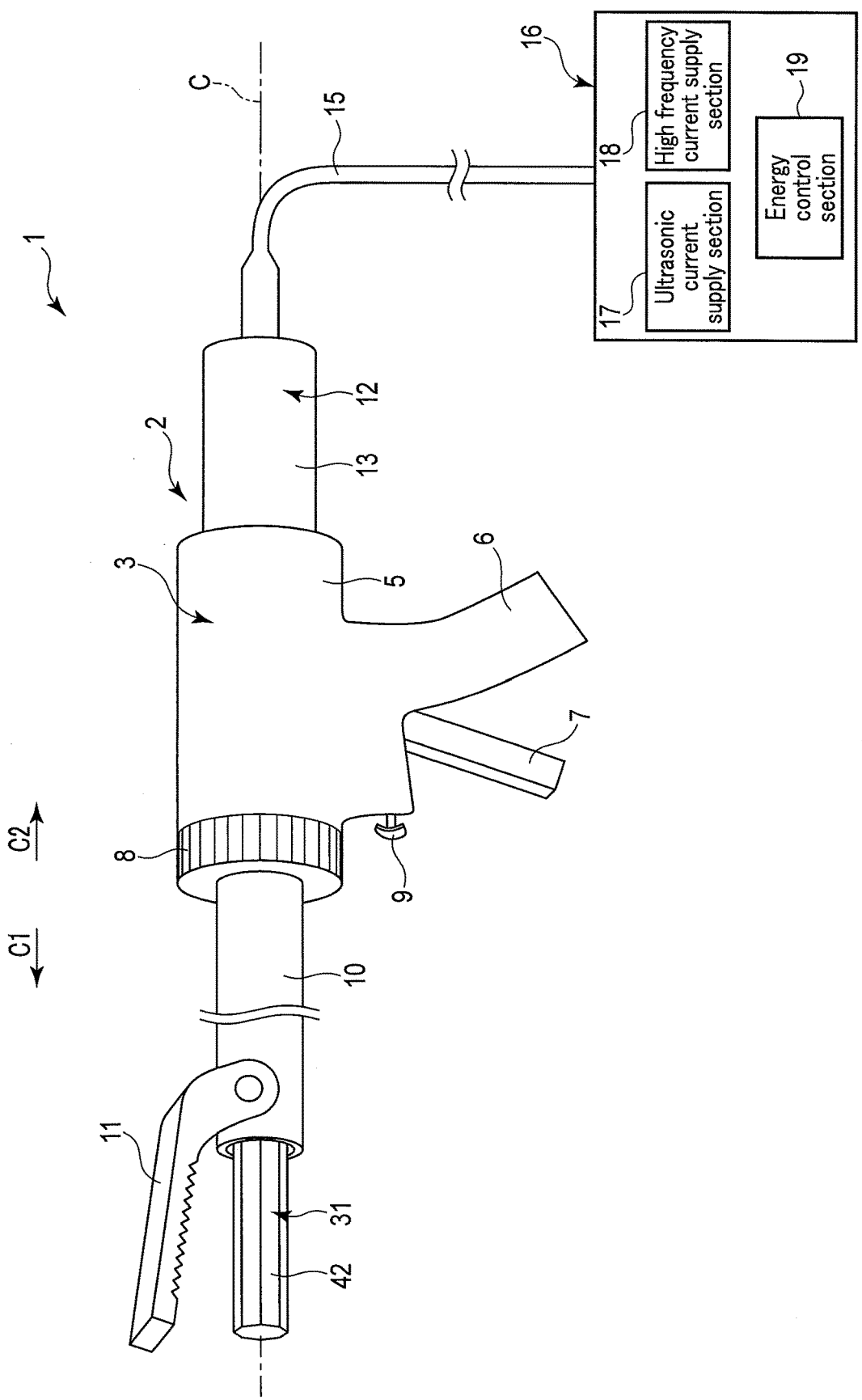
F I G. 1

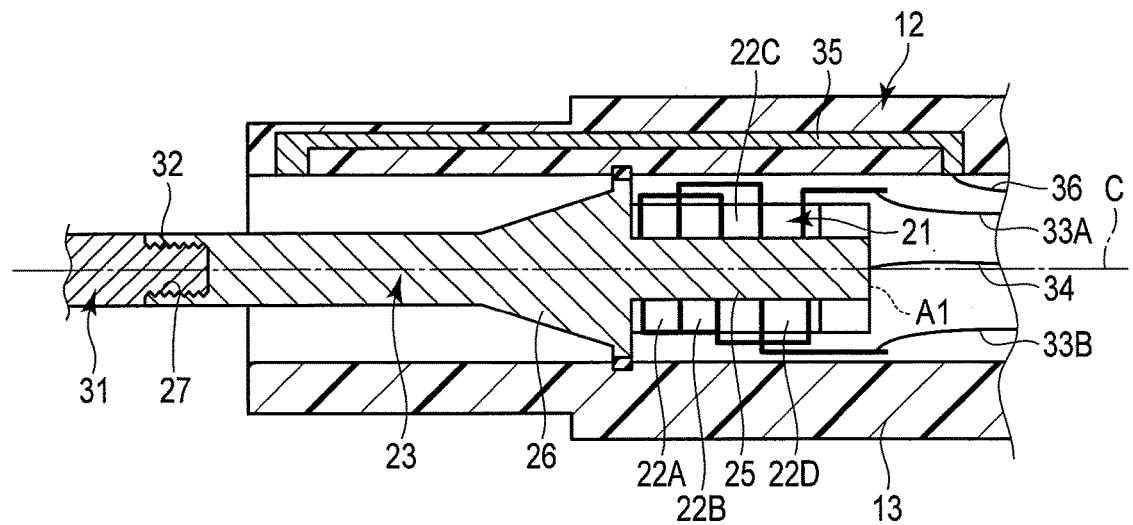
F I G. 2
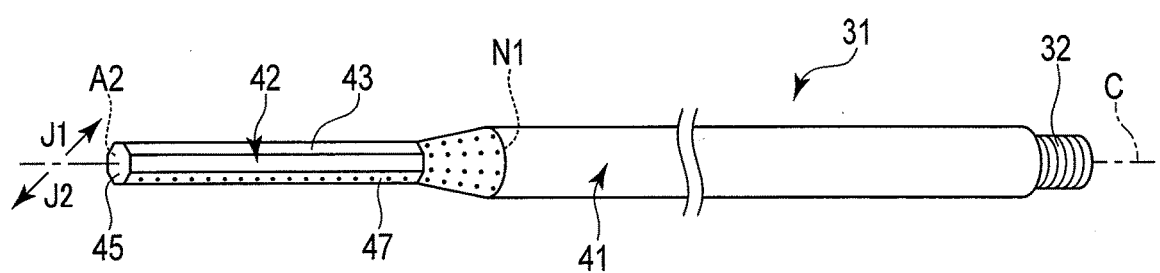
F I G. 3

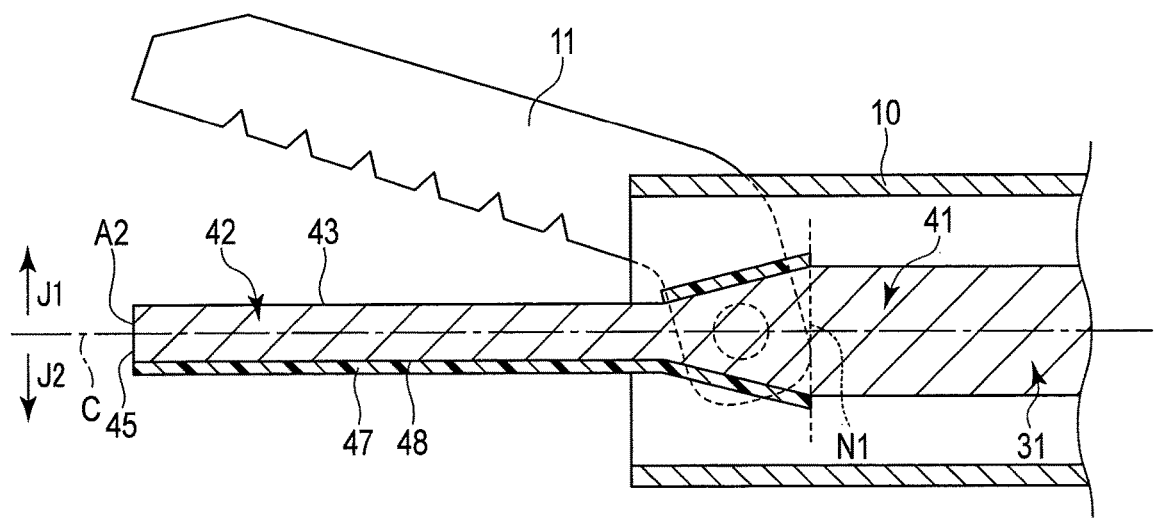
F I G. 4
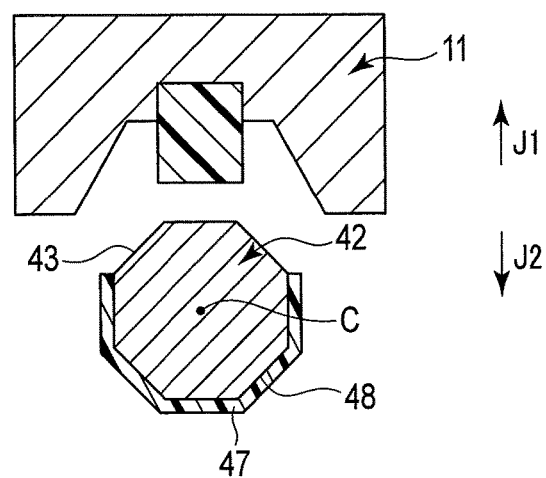
F I G. 5

| Type of surface finishing | Separation boundary value F0 of tensile force F | Elapsed time t until coating portion 47 peels off |
|---|---|---|
| Surface finishing × 1 | $3.92 \times 10^3$ N | 16 seconds |
| Surface finishing × 2 | $4.46 \times 10^3$ N | 119 seconds |
| Surface finishing × 3 | $5.81 \times 10^3$ N | 7200 seconds (2 hours) or more |

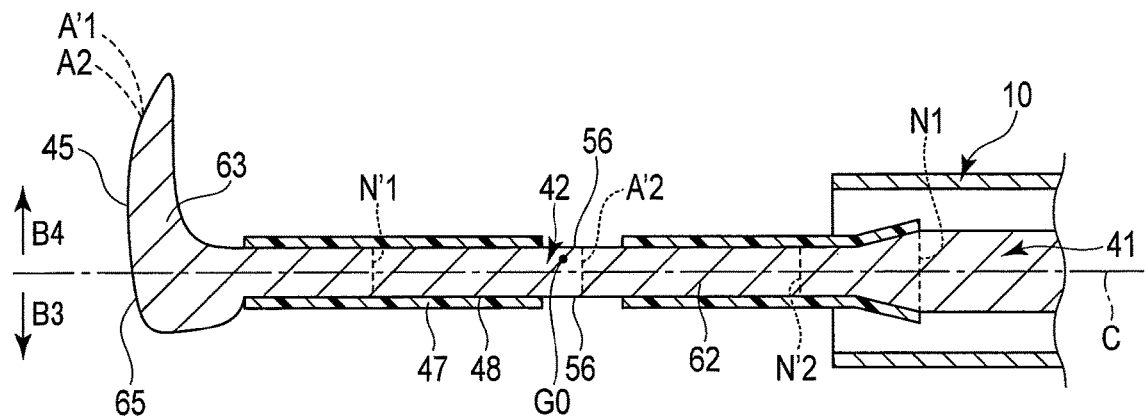
F I G. 14
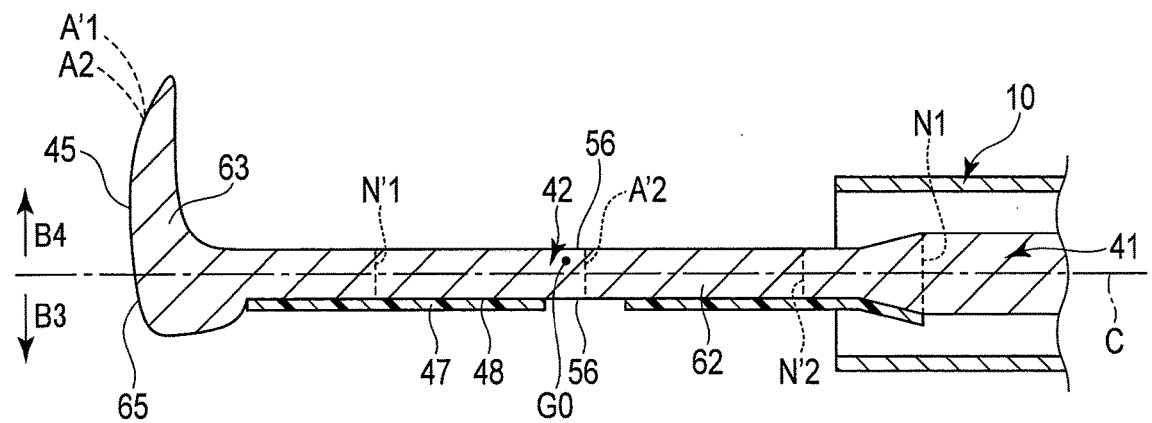
F I G. 15

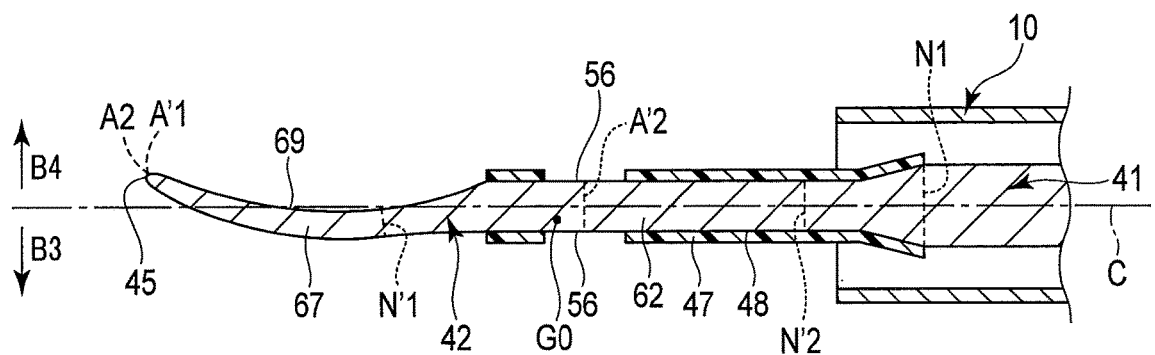
F I G. 16
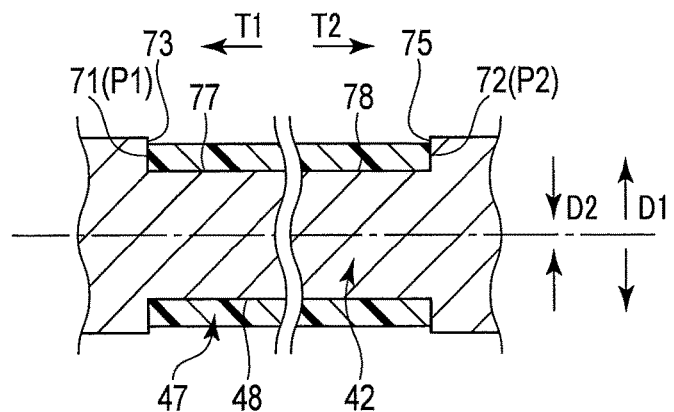
F I G. 17

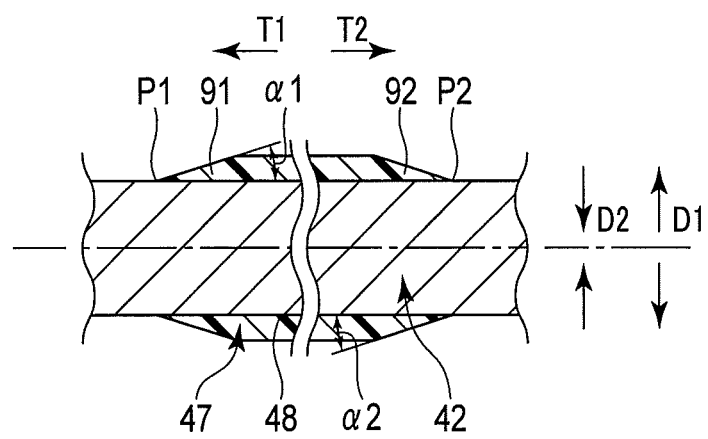
F I G. 22

ULTRASONIC TREATMENT APPARATUS

CROSS-REFERENCE TO RELATED APPLICATIONS

This is a Continuation Application of PCT Application No. PCT/JP2014/070869, filed Aug. 7, 2014 and based upon and claiming the benefit of priority from prior U.S. Provisional Application No. 61/863,104, filed Aug. 7, 2013, the entire contents of which are incorporated herein by reference.

BACKGROUND OF THE INVENTION

1. Field of the Invention

The present invention relates to an ultrasonic treatment apparatus including an ultrasonic probe configured to transmit an ultrasonic vibration from a proximal direction toward a distal direction.

2. Description of the Related Art

In Japanese Patent No. 3310532, there is disclosed an ultrasonic treatment apparatus including an ultrasonic probe configured to transmit an ultrasonic vibration from a proximal direction toward a distal direction along a longitudinal axis. In this ultrasonic treatment apparatus, a distal treatment section is provided in a distal portion of the ultrasonic probe. Additionally, in the ultrasonic treatment apparatus, a jaw which is openable and closable relative to the distal treatment section is provided. The distal treatment section vibrates by the ultrasonic vibration in a state where a treated object such as a biological tissue is grasped between the distal treatment section and the jaw, thereby treating the treated object. The distal treatment section includes a probe side facing surface which faces the jaw. In a state where the probe side facing surface that is a contact surface is in contact with the treated object, the treated object grasped between the jaw and the distal treatment section is treated.

BRIEF SUMMARY OF THE INVENTION

According to one aspect of the invention, an ultrasonic treatment apparatus includes that: a probe main body which is extended from a proximal direction toward a distal direction along a longitudinal axis, a high frequency electric power being configured to be supplied to the probe main body from a high frequency supply section, the probe main body being configured to transmit an ultrasonic vibration from the proximal direction toward the distal direction, thereby performing the vibration including a longitudinal vibration in a vibrating direction parallel to the longitudinal axis; a distal treatment section which is positioned on a distal direction side with respect to a most distal node position positioned most distally among node positions of the longitudinal vibration in the probe main body, the distal treatment section being configured to apply the ultrasonic vibration transmitted through the probe main body to a treated object, and the high frequency electric power being configured to be supplied to the distal treatment section through the probe main body, thereby the distal treatment section becoming a first electrode; a jaw which is openable and closable relative to the distal treatment section, the high frequency electric power being configured to be supplied to the jaw from the high frequency supply section, thereby becoming a second electrode different in potential from the first electrode in a position facing the first electrode so as to pass a high frequency current through the treated object grasped between the second electrode and the first electrode; a probe side facing surface provided in a position facing the jaw in a surface of the distal treatment section so that frictional heat is generated by the longitudinal vibration of the probe main body due to the ultrasonic vibration, and so that the high frequency current flowing between the first electrode and the second electrode passes through the grasped treated object; and a coating portion which is made of a material having electrically insulating properties and having a higher heat resistance than the probe main body, and which coats a surface facing a side opposite to the probe side facing surface in the probe main body so as to prevent the high frequency current from flowing from the first electrode into a biological tissue other than the treated object.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing a constitution of an ultrasonic treatment apparatus according to a first embodiment;

FIG. 2 is a cross-sectional view schematically showing a constitution of a transducer unit of a hand piece according to the first embodiment;

FIG. 3 is a perspective view schematically showing constitution of an ultrasonic probe according to the first embodiment;

FIG. 4 is a cross-sectional view schematically showing a constitution of a distal portion of the hand piece according to the first embodiment;

FIG. 5 is a cross-sectional view schematically showing a constitution of a distal treatment section and a jaw according to the first embodiment in a cross section perpendicular to a longitudinal axis;

FIG. 14 is a cross-sectional view schematically showing a constitution of a distal portion of an ultrasonic treatment instrument according to the third embodiment;

FIG. 15 is a cross-sectional view schematically showing a constitution of a distal portion of an ultrasonic treatment instrument according to a third modification;

FIG. 16 is a cross-sectional view schematically showing a constitution of a distal portion of an ultrasonic treatment instrument according to a fourth modification;

FIG. 17 is a schematic view showing a state where a finished surface in a distal treatment section according to a fourth embodiment is coated with a coating portion;

FIG. 22 is a schematic view showing a state where a finished surface in a distal treatment section according to an eighth modification is coated with a coating portion.

DETAILED DESCRIPTION OF THE INVENTION

First Embodiment

Figure 6:
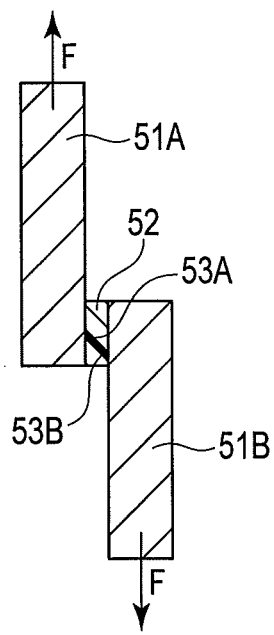
FIG. 6 is a schematic view showing a technique of measuring a close contact strength of a coating portion to a probe main body according to the first embodiment.

A first embodiment of the present invention will be described with reference to FIG. 1 to FIG. 8.

FIG. 1 is a view showing a constitution of an ultrasonic treatment apparatus 1 of the present embodiment. As shown in FIG. 1, the ultrasonic treatment device 1 includes a hand piece 2 that is an ultrasonic treatment instrument. The hand piece 2 has a longitudinal axis C. Here, one side of direction parallel to the longitudinal axis C is a distal direction (a direction of an arrow C1 of FIG. 1), and an opposite direction to the distal direction is a proximal direction (a direction of an arrow C2 of FIG. 1). Further, the distal direction and the proximal direction are longitudinal axial direction. The hand piece 2 is an ultrasonic coagulation-and-incision treatment instrument configured to coagulate and incise a treated object such as a biological tissue by use of an ultrasonic vibration. Additionally, the hand piece 2 is a high frequency treatment instrument configured to treat the treated object by use of a high frequency current.

The hand piece 2 includes a holding unit 3. The holding unit 3 includes a cylindrical case portion 5 extended along the longitudinal axis C, a fixed handle 6 formed integrally with the cylindrical case portion 5, and a movable handle 7 turnably attached to the cylindrical case portion 5. When the movable handle 7 turns about an attaching position to the cylindrical case portion 5, the movable handle 7 performs an opening movement or a closing movement relative to the fixed handle 6. Additionally, the holding unit 3 includes a rotating operation knob 8 to be attached to a distal direction side of the cylindrical case portion 5. The rotating operation knob 8 is rotatable relative to the cylindrical case portion 5 around the longitudinal axis C. Additionally, in the fixed handle 6, an energy operation input button 9 that is an energy operation input portion is provided.

The hand piece 2 includes a sheath 10 extended along the longitudinal axis C. When the sheath 10 is inserted from the distal side into an inside of the rotating operation knob 8 and an inside of the cylindrical case portion 5, the sheath 10 is attached to the holding unit 3. A jaw 11 is turnably attached to a distal portion of the sheath 10. The movable handle 7 is connected to a movable cylindrical portion (not shown) of the sheath 10 inside the cylindrical case portion 5. A distal end of the movable cylindrical portion is connected to the jaw 11. When the movable handle 7 is opened or closed to the fixed handle 6, the movable cylindrical portion moves along the longitudinal axis C. In consequence, the jaw 11 turns about the attaching position to the sheath 10. Additionally, the sheath 10 and the jaw 11 are rotatable integrally with the rotating operation knob 8 relative to the cylindrical case portion 5 about the longitudinal axis C.

Additionally, the hand piece 2 includes a transducer unit 12. The transducer unit 12 includes a transducer case 13 extended along the longitudinal axis C. When the transducer case 13 is inserted from a proximal direction side into the cylindrical case portion 5, the transducer case 13 is attached to the holding unit 3. In the cylindrical case portion 5, the transducer case 13 is coupled with the sheath 10. The transducer case 13 is rotatable integrally with the rotating operation knob 8 relative to the cylindrical case portion 5 around the longitudinal axis C. Additionally, the transducer case 13 is connected to one end of a cable 15. The other end of the cable 15 is connected to a control unit 16. The control unit 16 includes an ultrasonic current supply section 17, a high frequency current supply section 18, and an energy control section 19. Here, the ultrasonic current supply section 17 and the high frequency current supply section 18 includes an electric power source and an AC conversion circuit. Additionally, the energy control section 19 includes a CPU (a central processing unit) or an ASIC (an application specific integrated circuit) and a memory.

FIG. 2 is a view showing a constitution of the transducer unit 12. As shown in FIG. 2, the vibrator unit 12 comprises an ultrasonic transducer 21 that is an ultrasonic generating portion to which a current (an alternating current) is supplied so as to generate the ultrasonic vibration. The ultrasonic vibrator 21 is disposed inside the vibrator case 13. The ultrasonic transducer 21 includes (four in the present embodiment) piezoelectric elements 22A to 22D configured to convert the current into the vibration.

Additionally, inside the transducer case 13, a horn member 23 extended along the longitudinal axis C is disposed. The horn member 23 includes a transducer attaching portion 25. A member that forms the ultrasonic transducer 21 including the piezoelectric elements 22A to 22D and the like is attached to the transducer attaching portion 25. Additionally, a sectional area changing portion 26 is formed in the horn member 23. In the sectional area changing portion 26, a cross section perpendicular to the longitudinal axis C decreases toward the distal direction. By the sectional area changing portion 26, an amplitude of the ultrasonic vibration is enlarged. An internal thread portion 27 is provided in a distal portion of the horn member 23.

The hand piece 2 includes an ultrasonic probe 31 extended along the longitudinal axis C on the distal direction side of the horn member 23. As shown in FIG. 2, an external thread portion 32 is provided in a proximal portion of the ultrasonic probe 31. When the external thread portion 32 is screwed into the internal thread portion 27, the ultrasonic probe 31 is connected to the distal direction side of the horn member 23. The horn member 23 is extended up to the inside of the cylindrical case portion 5, and inside the cylindrical case portion 5, the ultrasonic probe 31 is connected to the horn member 23. The ultrasonic probe 31 is extended through an inside of the sheath 10, and projects from a distal end of the sheath 10 toward the distal direction.

The ultrasonic oscillator 21 is connected to one end of each of electric wires 33A and 33B. The other ends of the electric wires 33A and 33B are connected to the ultrasonic current supply section 17 of the control unit 16 through an inside of the cable 15. When an ultrasonic generating current is supplied from the ultrasonic current supply section 17 to the ultrasonic transducer 21 via the electric wires 33A and 33B, the ultrasonic vibration is generated in the ultrasonic vibrator 21. Further, the generated ultrasonic vibration is transmitted from the ultrasonic transducer 21 to the ultrasonic probe 31 via the horn member 23.

The horn member 23 is connected to one end of an electric wire 34. The other end of the electric wire 34 is connected to the high frequency current supply section 18 of the control unit 16 through the inside of the cable 15. Consequently, a probe side current path of a high frequency electric power to be supplied from the high frequency current supply section 18 is formed from the high frequency current supply section 18 through the electric wire 34 and the horn member 23 to the ultrasonic probe 31.

Additionally, in the transducer case 13, a conductive portion 35 is formed. The conductive portion 35 is connected to one end of an electric wire 36. The other end of the electric wire 36 is connected to the high frequency current supply section 18 of the control unit 16 through the inside of the cable 15. Additionally, in a state where the vibrator case 13 is coupled with the sheath 10, the sheath 10 is electrically connected to the conductive portion 35 of the transducer case 13. Consequently, a jaw side current path of the high frequency electric power to be supplied from the high frequency current supply section 18 is formed from the high frequency current supply section 18 through the electric wire 36, the conductive portion 35 of the vibrator case 13, and the sheath 10 to the jaw 11.

The energy control section 19 controls a supply state of the ultrasonic generating current from the ultrasonic current supply section 17 and a supply state of the high frequency current from the high frequency current supply section 18 on the basis of an input of an energy operation with the energy operation input button 9. Inside the fixed handle 6, a switch (not shown) is disposed. When the energy operation input button 9 is pressed and the energy operation is input, the switch is closed. The switch is electrically connected to the energy control section 19. When the switch is closed, an electric signal is transmitted to the energy control section 19, and the input of the energy operation is detected. When the input of the energy operation is detected, the ultrasonic generating current is supplied from the ultrasonic current supply section 17, and the high frequency current is supplied from the high frequency current supply section 18.

FIG. 3 is a view showing a constitution of the ultrasonic probe 31. FIG. 4 is a view showing a constitution of a distal portion of the hand piece 2. As shown in FIG. 3 and FIG. 4, the ultrasonic probe 31 includes a probe main body 41 extended along the longitudinal axis C. The probe main body 41 is made of, e.g., titanium. The ultrasonic vibration transmitted to the ultrasonic probe 31 is transmitted from the proximal direction toward the distal direction in the probe main body 41. The probe main body 41 transmits the ultrasonic vibration along the longitudinal axis C, thereby performing the vibration including a longitudinal vibration in a vibrating direction parallel to the longitudinal axis C. That is, in the probe main body 41, the ultrasonic vibration is transmitted, thereby performing at least the longitudinal vibration. Here, the probe main body 41, the horn member 23 and the ultrasonic transducer 21 become one vibrating body that performs the longitudinal vibration by the ultrasonic vibration generated in the ultrasonic transducer 21. Thus, a proximal end of the horn member 23 is a most proximal antinode position A1 positioned most proximally among antinode positions of the longitudinal vibration, and a distal end of the probe main body 41 (a distal end of the ultrasonic probe 31) is a most distal antinode position A2 positioned most distally among the antinode positions of the longitudinal vibration. It is to be noted that in the longitudinal vibration, a frequency is, e.g., 47 kHz, and an amplitude at the most distal antinode position A2 is, e.g., 80 µm. Additionally, a first vibrating direction that is one side of vibrating direction of the longitudinal vibration matches the distal direction, and a second vibrating direction that is the other side of the vibrating direction of the longitudinal vibration matches the proximal direction.

In a distal portion of the probe main body 41, a distal treatment section 42 is provided. The ultrasonic vibration is transmitted to the distal treatment section 42 via the probe main body 41, and in the distal treatment section 42, a treatment of a treated object such as the biological tissue is performed by using at least the ultrasonic vibration. The distal treatment section 42 is positioned on the distal direction side with respect to a most distal node position N1 positioned most distally among node positions of the longitudinal vibration. The ultrasonic probe 31, with the distal treatment section 42 projecting from the distal end of the sheath 10 toward the distal direction, is inserted through the sheath 10. Additionally, the most distal node position N1 of the longitudinal vibration is positioned inside the sheath 10.

When the jaw 11 turns relative to the sheath 10 by an opening or closing operation of the movable handle 7, the jaw 11 performs an opening movement or a closing movement relative to the distal treatment section 42. When the jaw 11 closes relative to the distal treatment section 42, the treated object is grasped between the jaw 11 and the distal treatment section 42. In a state where the treated object is grasped between the jaw 11 and the distal treatment section 42, the distal treatment section 42 longitudinally vibrates, thereby generating frictional heat between the distal treatment section 42 and the treated object. The treated object is coagulated and incised by the frictional heat.

Additionally, the high frequency electric power supplied from the high frequency current supply section 18 through the probe side current path to the ultrasonic probe 31 is supplied from the proximal direction toward the distal direction in the probe main body 41. When the high frequency electric power is supplied through the probe main body 41 to the distal treatment section 42, the distal treatment section 42 functions as a first electrode. The distal treatment section 42 treats the treated object by use of the high frequency current in addition to the ultrasonic vibration. Additionally, when the high frequency electric power is supplied from the high frequency current supply section 18 through the jaw side current path to the jaw 11, the jaw 11 functions as a second electrode that is different in electric potential from the first electrode. In the state where the treated object is grasped between the jaw 11 and the distal treatment section 42, the high frequency electric power is supplied to the jaw 11 and the distal treatment section 42, and hence the high frequency current flows through the treated object. Consequently, the treated object is denatured, and the coagulation of the treated object is promoted.

FIG. 5 is a view showing the distal treatment section 42 and the jaw 11 in a cross section perpendicular to the longitudinal axis C. It is to be noted that in FIG. 3 to FIG. 5, a direction of an arrow J1 is an opening direction of the jaw 11, and a direction of an arrow J2 is a closing direction of the jaw 11. As shown in FIG. 3 to FIG. 5, the cross section of the distal treatment section 42 which is perpendicular to the longitudinal axis C is substantially formed into an octagonal shape. Additionally, in the distal treatment section 42, there is provided a probe side facing surface 43 which faces toward the opening direction of the jaw 11 and faces the jaw 11. In the state where the treated object is grasped between the jaw 11 and the distal treatment section 42, the treated object comes in contact with the probe side facing surface 43. That is, the probe side facing surface 43 becomes a contact surface to be brought into contact with the treated object in the treatment.

Additionally, the distal treatment section 42 includes a probe distal surface 45 that forms the distal end of the probe main body 41 (the distal end of the ultrasonic probe 31). The probe distal surface 45 is not parallel to the longitudinal axis C. That is, the probe distal surface 45 is not parallel to the vibrating direction of the longitudinal vibration. The probe distal surface 45 that is not parallel to the vibrating direction of the longitudinal vibration longitudinally vibrates, pressurization and decompression are periodically repeated in the vicinity of the probe distal surface 45. The distal end of the probe main body 41 is the most distal antinode position A2 that is one of the antinode positions of the longitudinal vibration, and hence, the amplitude of the longitudinal vibration in the probe distal surface 45 increases. The amplitude of the longitudinal vibration in the probe distal surface 45 increases, and hence, a pressurizing and decompressing effect increases in the vicinity of the probe distal surface 45. Further, the distal treatment section 42 longitudinally vibrates in a liquid or in a state where the liquid is present in the vicinity of the probe distal surface 45, and hence, in the vicinity of the probe distal surface 45 in which the pressurizing and decompressing effect caused by the longitudinal vibration increases, cavities are generated in the liquid by the pressurizing and decompressing action. The generated cavities disappear by a force that acts in the decompression of the vicinity of the probe distal surface 45. Thus, the cavities disappear, and hence, large impact energy is generated. The abovementioned phenomenon is called a cavitation phenomenon.

In the cavitation phenomenon that occurs in the present embodiment, the probe distal surface 45 that is not parallel to the vibrating direction of the longitudinal vibration becomes a cavitation generating surface configured to generate the cavities in the liquid by the pressurizing and decompressing effect. Additionally, the cavitation phenomenon occurs only in a case where the probe distal surface 45 is longitudinally vibrated at a reference amplitude V0 or more. Therefore, in a case where the probe distal surface 45 is longitudinally vibrated at an amplitude smaller than the reference amplitude V0, the cavities are not generated in the liquid in the vicinity of the probe distal surface 45. It is to be noted that the reference amplitude V0 is smaller than 80 µm, and therefore in the treatment of the treated object in which the ultrasonic vibration (the longitudinal vibration) is used in this embodiment, the cavitation phenomenon occurs by the probe distal surface 45.

In the distal treatment section 42, the whole surface, other than the probe side facing surface 43 that is the contact surface and the probe distal surface 45 that is the cavitation generating surface, is coated with a coating portion 47. In the present embodiment, a dotted region shown in FIG. 3 is coated with the coating portion 47. The coating portion 47 is made of a material having a higher heat resistance than the probe main body 41. Additionally, the coating portion 47 is made of an electrically insulating material. The coating portion 47 is made of, e.g., a resin, and in the present embodiment, a polyether ether ketone (PEEK), an imide-modified epoxy resin or a polyimide having a high biocompatibility is used as the material of the coating portion 47.

Additionally, the surface coated with the coating portion 47 in the distal treatment section 42 becomes a treated surface 48 which is to be subjected to surface treating. In the present embodiment, the surface of the distal treatment section 42 other than the probe side facing surface 43 and the probe distal surface 45 becomes the finished surface 48. The finished surface 48 is subjected to the surface finishing in which a surface roughness is heightened by sand blast. Further, the finished surface 48 is coated with the coating portion 47 in a state where the surface finishing is performed. By the surface treating, an oxide film is removed, and an anchoring effect is exerted between the finished surface 48 and the coating portion 47. In consequence, by the surface finishing of the finished surface 48, a close contact strength of the coating portion 47 relative to the finished surface 48 in the probe main body 41 heightens. In the treated surface 48, the surface finishing is performed so that the surface is coated with the coating portion 47 at a close contact strength of $1.33 \times 10^7$ N/m$^2$ or more.

Here, the close contact strength of the coating portion 47 will be described. FIG. 6 is a view showing a technique of measuring the close contact strength of the coating portion 47. As shown in FIG. 6, the measuring of the close contact strength of the coating portion 47 is performed in a state where a first test piece 51A and a second test piece 51B made of the same material (e.g., titanium) as in the probe main body 41 are bonded via a bonding member 52 made of the same material (e.g., PEEK) as in the coating portion 47. The first test piece 51A includes a first close contact surface 53A which comes in contact closely with the bonding member 52, and the second test piece 51B includes a second close contact surface 53B which comes in contact closely with the bonding member 52. Therefore, the first close contact surface 53A of the first test piece 51A and the second close contact surface 53B of the second test piece 51B are bonded by the bonding member 52. It is to be noted that the first close contact surface 53A and the second close contact surface 53B have the same area S0 with respect to each other.

In a state where the first test piece 51A and the second test piece 51B are bonded via the bonding member 52, the first test piece 51A and the second test piece 51B are pulled, thereby measuring the close contact strength of the coating portion 47. The first test piece 51A and the second test piece 51B are pulled in opposite directions with respect to each other with tensile forces F having the same size with respect to each other. When the tensile force F of the first test piece 51A and the second test piece 51B increases, the first test piece 51A is separated from the second test piece 51B against a bonding force by the bonding member 52. The first test piece 51A is separated from the second test piece 51B in a case where a size of the tensile force F of the first test piece 51A and the second test piece 51B is a separation boundary value F0 or more.

The close contact strength of the coating portion 47 is calculated by using the separation boundary value F0 of the tensile force F of the first test piece 51A and the second test piece 51B, and the area S0 of each of the first close contact surface 53A and the second close contact surface 53B. That is, in a case where the close contact strength of the coating portion 47 is I0, the following equation is established.

[Equation 1]

$$I0 = \frac{F0}{S0} \quad (1)$$

Additionally, the first close contact surface 53A and the second close contact surface 53B are subjected to surface finishing to heighten a surface roughness in the same manner as in the finished surface 48 in the distal treatment section 42. The first test piece 51A and the second test piece 51B are bonded via the bonding member 52 in a state where the first close contact surface 53A and the second close contact surface 53B are subjected to the surface finishing. The first close contact surface 53A and the second close contact surface 53B that come in contact closely with the bonding member 52 are subjected to the surface treating, and hence, the bonding force between the first test piece 51A and the second test piece 51B by the bonding member 52 increases due to an anchoring effect between the bonding member 52 and each of the first close contact surface 53A and the second close contact surface 53B, or the like. Consequently, the separation boundary value F0 of the tensile force F of the first test piece 51A and the second test piece 51B increases, and the close contact strength I0 increases.

The close contact strength I0 is measured for each of cases where types of surface finishing to be performed on the first close contact surface 53A and the second close contact surface 53B are different from one another. Further, the close contact strength I0 is acquired as measurement data concerning a case where the surface finishing X1 is performed on the first close contact surface 53A and the second close contact surface 53B, a case where surface finishing X2 is performed on the first close contact surface 53A and the second close contact surface 53B, and a case where surface finishing X3 is performed on the first close contact surface 53A and the second close contact surface 53B. The type of surface finishing to be performed on the first close contact surface 53A and the second close contact surface 53B varies, thereby changing the separation boundary value F0 of the tensile force F of the first test piece 51A and the second test piece 51B, and hence the close contact strength I0 changes. It is to be noted that in after-mentioned measurement, the area S0 of each of the first close contact surface 53A and the second close contact surface 53B is defined as $3 \times 10^{-4}$ m$^2$ (3 cm$^2$), and the close contact strength I0 is measured. Additionally, the surface finishing X1 is the surface finishing by the sand blast in which glass beads of a grain size No. 320 are used as media (sand). The surface finishing X2 is the surface finishing by the sand blast in which glass beads of a grain size No. 220 are used as the media. Further, the surface finishing X3 is the surface treating by the sand blast in which alundum of a grain size No. 320 is used as the media.

Figure 7:
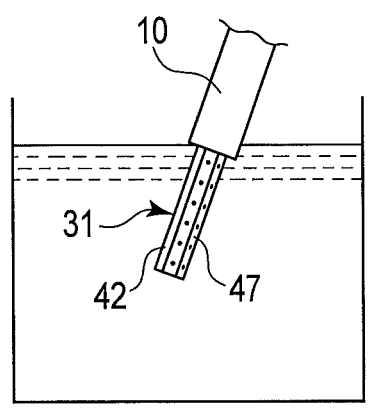
FIG. 7 is a schematic view showing a method of measuring an elapsed time until the coating portion peels off from the probe main body in a case where the probe main body according to the first embodiment is vibrated.

FIG. 7 is a view showing a method of measuring an elapsed time t until the coating portion 47 peels off from the probe main body 41 in a case where the probe main body 41 is vibrated. As shown in FIG. 7, in the case where the probe main body 41 is vibrated, the measuring of the elapsed time t until the coating portion 47 peels off from the probe main body 41 is performed in a state where the distal treatment section 42 is positioned in a liquid such as water. In the distal treatment section 42, the finished surface 48 is coated with the coating portion 47. Further, the probe main body 41 is vibrated by the ultrasonic vibration in the state where the distal treatment section 42 is positioned in the water, and there is measured the elapsed time t from the start of the vibration until the coating portion 47 peels off from the probe main body 41 (the distal treatment section 42). It is to be noted that the measuring of the elapsed time t until the coating portion 47 peels off is preferably performed in a state where the jaw 11 is not attached to the sheath 10 as in FIG. 7. Additionally, FIG. 7 shows the coating portion 47 in a dotted manner.

In the treatment using the ultrasonic vibration, the treated object might be treated in a state where the distal treatment section 42 is positioned in a liquid such as blood or a body fluid. When the probe main body 41 is vibrated in the state where the distal treatment section 42 is positioned in the liquid, a liquid resistance acts on the coating portion 47, and hence, an external load due to the vibration which acts on the coating portion 47 increases. Thus, in the case where the probe main body 41 is vibrated in the state where the distal treatment section 42 is positioned in the liquid, the coating portion 47 is easier to peel off from the probe main body 41 as compared with a case where the probe main body 41 is vibrated in a state where the distal treatment section 42 is positioned in air. Time for which the distal treatment section 42 is vibrated in the liquid in the treatment varies with the type of treatment, a use application of the hand piece 2, or the like, but the distal treatment section 42 might be vibrated in the liquid for several tens of seconds. Therefore, also in a case where the distal treatment section is vibrated in the liquid for several tens of seconds, the finished surface 48 in the distal treatment section 42 is coated with the coating portion 47 at a close contact strength to such an extent that the coating portion does not peel off from the probe main body 41.

The elapsed time t until the coating portion 47 peels off is measured for each of the cases where the types of surface finishing to be performed on the finished surface 48 are different from one another. Further, the elapsed time t until the coating portion 47 peels off is acquired as measurement data concerning each of the case where the surface finishing X1 mentioned above is performed on the finished surface 48, a case where the surface finishing X2 mentioned above is performed on the finished surface 48, and a case where the surface finishing X3 mentioned above is performed on the finished surface 48. Thus, the type of surface finishing to be performed on the finished surface 48 varies, thereby changing the close contact strength I0 of the coating portion 47 onto the finished surface 48, and hence, the elapsed time t until the coating portion 47 peels off changes. It is to be noted that in after-mentioned measurement, the probe main body 41 in the state where the distal treatment section 42 is positioned in the water is longitudinally vibrated at a frequency of 47 kHz and an amplitude of 80 μm at the most distal antinode position A2, and hence, the elapsed time t until the coating portion 47 peels off is measured.

Figures 8, 9:
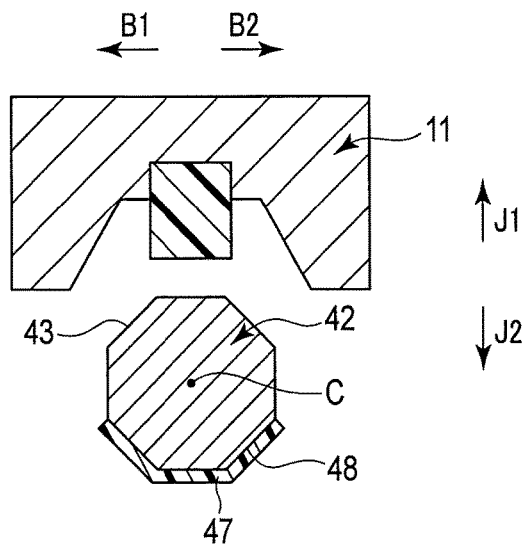
FIG. 8 is a schematic view showing measurement data of a separation boundary value of a tensile force of a first test piece and a second test piece according to the first embodiment, and an elapsed time from the start of the vibration until the coating portion peels off in water.
FIG. 9 is a cross-sectional view schematically showing a constitution of a distal treatment section and a jaw according to a first modification in a cross section perpendicular to a longitudinal axis.

FIG. 8 is a view showing the measurement data of the separation boundary value F0 of the tensile force F of the first test piece 51A and the second test piece 513, and the elapsed time t from the start of the vibration until the coating portion 47 peels off in the water. As shown in FIG. 8, in the case where the surface finishing X1 is performed, the separation boundary value F0 of the tensile force F is $3.92 \times 10^3$ N. Further, the elapsed time t from the start of the vibration until the coating portion 47 peels off is 16 seconds. In the case where the surface finishing X2 is performed, the separation boundary value F0 of the tensile force F is $4.46 \times 10^3$ N. Further, the elapsed time t from the start of the vibration until the coating portion 47 peels off in the water is 119 seconds. Additionally, in the case where the surface finishing X3 is performed, the separation boundary value F0 of the tensile force F is $5.58 \times 10^3$ N. Further, even in a case where the distal treatment section 42 is vibrated for 7200 seconds (two hours) in the water, the coating portion 47 does not peel off. That is, in the case where the surface finishing X3 is performed, the elapsed time t from the start of the vibration until the coating portion 47 peels off is longer than 7200 seconds.

According to the abovementioned measurement data, the close contact strength I0 of the coating portion 47 heightens in the case where the surface finishing X2 is performed as compared with the case where the surface finishing X1 is performed. Additionally, in the case where the surface finishing X3 is performed, the close contact strength I0 of the coating portion 47 heightens as compared with the case where the surface finishing X2 is performed. It is to be noted that also when the surface finishing X1 in which the close contact strength I0 of the coating portion 47 is lowest among the surface finishing X1 to X3 is performed on the finished surface 48, the coating portion 47 does not peel off from the probe main body 41 even after the elapse of a long time in the vibration in the state where the distal treatment section 42 is positioned in the air. That is, also when the surface finishing X1 is performed, the coating portion 47 does not peel off even after the elapse of several hours or more from the start of the vibration, as long as the probe main body 41 vibrates in a state where the distal treatment section 42 is positioned in the air.

As described above, it is necessary to coat the finished surface 48 in the distal treatment section 42 with the coating portion 47 at a close contact strength to such an extent that the coating portion does not peel off from the probe main body 41, also in the case where the probe main body is vibrated in the liquid for several tens of seconds. Thus, according to the measurement data, it is necessary to set the separation boundary value F0 of the tensile force F to $4 \times 10^3$ N or more. Here, in the abovementioned measurement, the area S0 of each the first close contact surface 53A and the second close contact surface 53B is defined as $3 \times 10^{-4}$ m$^2$, and hence, when the separation boundary value F0 is $4 \times 10^3$ N, the close contact strength TO of the coating portion 47 is $1.33 \times 10^7$ N/m$^2$ in accordance with Equation (1). Therefore, it is necessary to set the close contact strength TO of the coating portion 47 onto the probe main body 41 to $1.33 \times 10^7$ N/m$^2$ or more so that the coating portion 47 does not peel off from the probe main body 41 also in the case where the probe main body is vibrated in the liquid for several tens of seconds. That is, it is necessary to perform the surface finishing of the finished surface 48 in a state where the finished surface is coated with the coating portion 47 at the close contact strength of $1.33 \times 10^7$ N/m$^2$ or more.

Next, an function and an effect of the ultrasonic probe 31 and the ultrasonic treatment apparatus 1 will be described. In a case where a treated object such as the biological tissue is treated by using the ultrasonic treatment device 1, the treated object is grasped between the distal treatment section 42 and the jaw 11. Further, when the energy operation is input by the energy operation input button 9 in the state where the treated object is grasped, the ultrasonic generating current is supplied from the ultrasonic current supply section 17, and the high frequency current is supplied from the high frequency current supply section 18. When the ultrasonic generating current is supplied to the ultrasonic transducer 21, the ultrasonic vibration is generated. The generated ultrasonic vibration is transmitted to the ultrasonic probe 31, and transmitted up to the distal treatment section 42 along the longitudinal axis C in the probe main body 41. When the ultrasonic vibration is transmitted, the probe main body 41 performs the vibration including the longitudinal vibration in the vibrating direction parallel to the longitudinal axis C. The distal treatment section 42 longitudinally vibrates in the state where the treated object is grasped between the jaw 11 and the distal treatment section 42, thereby generating the frictional heat between the distal treatment section 42 and the treated object. By the frictional heat, the treated object is coagulated and simultaneously incised.

Additionally, the high frequency electric power is supplied to the jaw 11 and the distal treatment section 42. When the high frequency electric power is supplied to the jaw 11 and the distal treatment section 42 in the state where the treated object is grasped between the jaw 11 and the distal treatment section 42, the high frequency current flows through the treated object. In consequence, the treated object is denatured, and the coagulation of the treated object is promoted.

In the treatment using the ultrasonic vibration, heat is generated in the probe main body 41 by the vibration. By the generation of the heat, a temperature rises also in the finished surface 48 which is different from the probe side facing surface 43 as the contact surface in the distal treatment section 42. In the present embodiment, the finished surface 48 which is the surface other than the probe side facing surface 43 and the probe distal surface 45 in the distal treatment section 42 is coated with the coating portion 47. Further, the coating portion 47 is made of a material having a higher heat resistance than the probe main body 41. The coating portion 47 has the high heat resistance, and hence, even in a case where the distal treatment section 42 reaches a high temperature, the coating portion 47 does not reach the high temperature. Thus, the coating portion 47 is disposed, and hence, even in a case where the ultrasonic probe 31 comes in contact with the biological tissue in a region other than the treated object in the treatment, the coating portion 47 that does not reach the high temperature comes in contact with the biological tissue in the region other than the treatment object. Consequently, heat damage of the biological tissue in the region other than the treatment object can effectively be prevented, and a treatment performance in the treatment using the ultrasonic vibration can be secured.

Additionally, the coating portion 47 is made of an electrically insulating material. Thus, the coating portion 47 is provided, and hence, also in the case where the ultrasonic probe 31 comes in contact with the biological tissue in the region other than the treated object in the treatment, the coating portion 47 having electrically insulating properties comes in contact with the biological tissue in the region other than the treated object. The coating portion 47 has the insulating properties, and hence, in the case where the coating portion 47 comes in contact with the biological tissue in the region other than the treated object, the high frequency current is not supplied from the distal treatment section 42 to the biological tissue other than the treated object via the coating portion 47. The supply of the high frequency current from the distal treatment section 42 to the biological tissue other than the treated object is prevented, thereby heightening a current density of the high frequency current that flows through the treated object grasped between the distal treatment section 42 and the jaw 11. In consequence, the treatment performance in the treatment using the high frequency current can improve.

In addition, the coating portion 47 is made of a PEEK, an imide-modified epoxy resin or a polyimide having a high biocompatibility. Consequently, even during a treatment in a state that the coating portion 47 is positioned in a living body, influence of the coating portion 47 onto the living body can be alleviated.

Additionally, in the treatment using the ultrasonic vibration, the distal treatment section 42 might be vibrated in a liquid such as the blood. In the finished surface 48, the surface finishing is performed in a state where the finished surface is coated with the coating portion 47 at a close contact strength of $1.33 \times 10^7$ N/m$^2$ or more. Consequently, when the probe main body 41 whose distal treatment section 42 is positioned in the liquid is vibrated by the longitudinal vibration having a frequency of 47 kHz and an amplitude of 80 μm at the most distal antinode position A2 for use in the treatment by the ultrasonic vibration, the coating portion 47 does not peel off from the finished surface 48 in the distal treatment section 42 even after the elapse of several tens of seconds from the start of the vibration. Therefore, in the treatment using the ultrasonic vibration in the state where the distal treatment section 42 is positioned in the liquid in which the external load due to the vibration increases, the coating portion 47 can effectively be prevented from peeling off from the distal treatment section 42.

Additionally, the probe distal surface 45 that is the cavitation generating surface is not coated with the coating portion 47. In the cavitation phenomenon, the cavities are generated in the liquid, and the generated cavities disappear, thereby generating the impact energy. The impact energy to be generated by the disappearance of the cavities is large, and even in a case where the probe distal surface 45 is coated with the coating portion 47 at a close contact strength of $1.33 \times 10^7$ N/m$^2$ or more, the coating portion 47 peels off from the probe distal surface 45 due to the impact energy. In the present embodiment, the probe distal surface 45 is not coated with the coating portion 47, and hence the peeling of the coating portion 47 due to the cavitation phenomenon can effectively be prevented.

Modification of First Embodiment

In the first embodiment, in the distal treatment section 42, the whole surface, other than the probe side facing surface 43 as the contact surface and the probe distal surface 45 as the cavitation generating surface, is coated with the coating portion 47, but it is not limited to this embodiment. For example, in a first modification that is a modification of the first embodiment, as shown in FIG. 9, a part of a surface other than a probe side facing surface 43 and a probe distal surface 45 in a distal treatment section 42 may be coated with a coating portion 47.

According to the present modification, in the distal treatment section 42, as to the surface other than the probe side facing surface 43 and the probe distal surface 45, the surface toward a closing direction (a direction of an arrow J2 of FIG. 9) of a jaw 11 is only coated with the coating portion 47. Here, one side of direction perpendicular to (intersecting) a longitudinal axis C and perpendicular to opening and closing direction (a direction of an arrow J1 of FIG. 9 and the direction of the arrow J2) of the jaw 11 is defined as a first width direction (a direction of an arrow B1 of FIG. 9), and an opposite side to the first width direction is defined as a second width direction (a direction of an arrow B2 of FIG. 9). According to the present modification, in the distal treatment section 42, as to the surfaces other than the probe side facing surface 43 and the probe distal surface 45, the surface directed in the first width direction and the surface toward the second width direction are not coated with the coating portion 47. Also in the present modification, the surface to be coated with the coating portion 47 is a finished surface 48 which is to be subjected to surface finishing so that the surface is coated with the coating portion 47 at a close contact strength of $1.33 \times 10^7$ N/m$^2$ or more.

Figure 10:
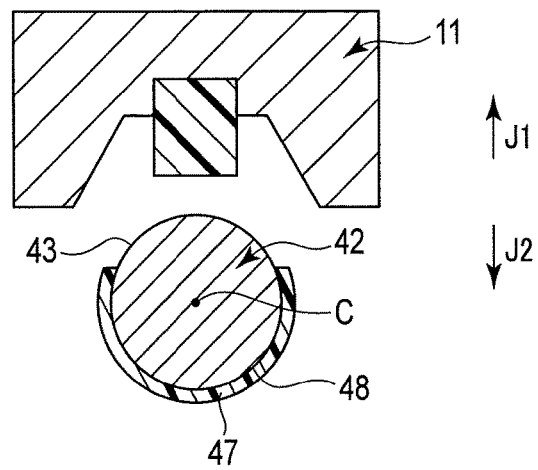
FIG. 10 is a cross-sectional view schematically showing a constitution of a distal treatment section and a jaw according to a second modification in a cross section perpendicular to a longitudinal axis.

Additionally, in the first embodiment, the cross section of the distal treatment section 42 which is perpendicular to the longitudinal axis C is substantially formed into an octagonal shape, but it is not limited to this embodiment. For example, in a second modification that is another modification of the first embodiment, as shown in FIG. 10, a cross section of a distal treatment section 42 which is perpendicular to a longitudinal axis C may substantially be formed into a round shape. According to the present modification, in the distal treatment section 42, the whole surface, other than a probe side facing surface 43 as a contact surface and a probe distal surface 45 as a cavitation generating surface, is coated with a coating portion 47. Also in the present modification, the surface to be coated with the coating portion 47 is a finished surface 48 which is to be subjected to surface finishing so that the surface is coated with the coating portion 47 at a close contact strength of $1.33 \times 10^7$ N/m$^2$ or more. It is to be noted that also in the case where the cross section of the distal treatment section 42 which is perpendicular to the longitudinal axis C is substantially formed into the round shape, a part of the surface other than the probe side facing surface 43 and the probe distal surface 45 in the distal treatment section 42 may be coated with the coating portion 47.

According to the abovementioned first embodiment, first modification and second modification, in the distal treatment section 42, at least a part of the surface other than the probe side facing surface 43 as the contact surface and the probe distal surface 45 as the cavitation generating surface may be coated with the coating portion 47. The coating portion 47 may be made of a material having a higher heat resistance than the probe main body 41. Furthermore, the surface to be coated with the coating portion 47 may be the finished surface 48 which is to be subjected to the surface finishing in which the surface is coated with the coating portion 47 at the close contact strength of $1.33 \times 10^7$ N/m$^2$ or more.

Second Embodiment

Next, a second embodiment of the present invention will be described with reference to FIG. 11 and FIG. 12. In the second embodiment, the constitution of the first embodiment is modified as follows. It is to be noted that the same part as in the first embodiment is denoted with the same reference sign, and the description is omitted.

Figure 11:
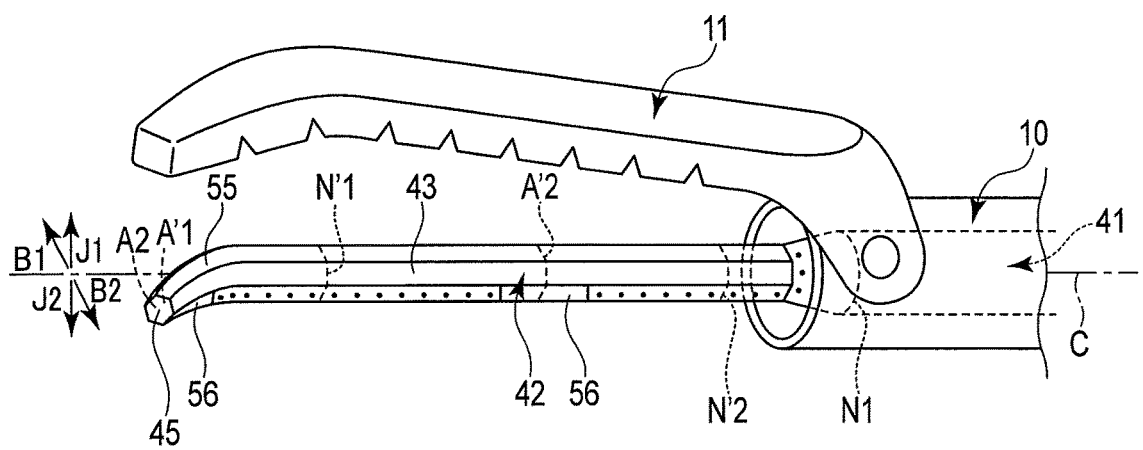
FIG. 11 is a perspective view schematically showing a constitution of a distal portion of a hand piece according to a second embodiment.

FIG. 11 is a view showing a constitution of a distal portion of a hand piece 2 that is an ultrasonic treatment instrument according to the present embodiment. As shown in FIG. 11, in the present embodiment, a distal treatment section 42 of an ultrasonic probe 31 includes a probe curved portion 55 curved with respect to a longitudinal axis C from a first width direction (a direction of an arrow B1 of FIG. 11)

toward a second width direction (a direction of an arrow B2 of FIG. 11). Thus, the probe curved portion 55 is provided in the distal treatment section 42, and hence, visibility of an operator improves in a treatment. Here, the first width direction matches a first perpendicular direction (a first intersecting direction) that is one of directions perpendicular to (intersecting) the longitudinal axis C, and the second width direction matches a second perpendicular direction (a second intersecting direction) that is an opposite side to the first perpendicular direction. The first width direction and the second width direction are perpendicular to an opening and closing direction of a jaw 11 (a direction of an arrow J1 of FIG. 11 and a direction of an arrow J2).

Figure 12:
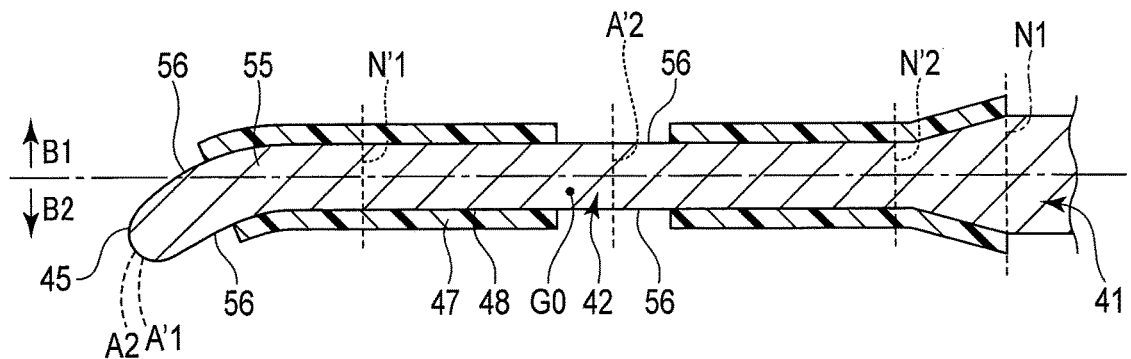
FIG. 12 is a cross-sectional view schematically showing a distal treatment section according to the second embodiment in a cross section perpendicular to an opening and closing direction of a jaw.

FIG. 12 is a view showing the distal treatment section 42 in a cross section perpendicular to the opening and closing direction of the jaw 11. As shown in FIG. 11 and FIG. 12, the probe curved portion 55 is provided, and hence, a gravity center G0 of the distal treatment section 42 is positioned on a second width direction side (a second perpendicular direction side) with respect to the longitudinal axis C. In the first width direction and the second width direction, the gravity center G0 of the distal treatment section 42 is positioned away from the longitudinal axis C, and hence, a probe main body 41 transmits an ultrasonic vibration along the longitudinal axis C, thereby performing a transverse vibration in a vibrating direction parallel to the first width direction and the second width direction in addition to the abovementioned longitudinal vibration. An antinode position A'1 positioned most distally among the antinode positions of the transverse vibration is positioned at a distal end of the probe main body 41 (a distal end of the ultrasonic probe 31). Additionally, a frequency of the transverse vibration is larger than a frequency of the longitudinal vibration, and hence, a wavelength of the transverse vibration is shorter than a wavelength of the longitudinal vibration. Consequently, the antinode position A'1 and an antinode position A'2 and node positions N'1 and N'2 of the transverse vibration are positioned in the distal treatment section 42, and positioned on the distal direction side with respect to a most distal node position N1 of the longitudinal vibration. Here, the antinode position A'2 of the transverse vibration is positioned second distally among the antinode positions of the transverse vibration. Additionally, the node position N'1 of the transverse vibration is positioned most distally among the node positions of the transverse vibration, and the node position N'2 of the transverse vibration is positioned second distally among the node positions of the transverse vibration.

In the present embodiment, the probe main body 41 transversely vibrates, and hence, in the distal treatment section 42, a cavitation phenomenon caused by the transverse vibration also occurs in addition to a cavitation phenomenon caused by the longitudinal vibration of a probe distal surface 45. This cavitation caused by the transverse vibration occurs, when a surface that is not parallel to a vibrating direction of the transverse vibration transversely vibrates at an amplitude of a reference amplitude V0 or more. That is, an outer peripheral generating surface 56 that faces toward the first width direction (the first perpendicular direction) or the second width direction (the second perpendicular direction) and that transversely vibrates at the amplitude of the reference amplitude V0 or more is provided as a cavitation generating surface in the distal treatment section 42. The outer peripheral generating surface 56 is positioned in the vicinity of the antinode positions A'1 and A'2 of the transverse vibration where the amplitude of the transverse vibration increases, in a longitudinal axis direction parallel to the longitudinal axis C. That is, the outer peripheral generating surface 56 is positioned at a position different from the node positions N'1 and N'2 of the transverse vibration where the amplitude of the transverse vibration becomes zero, in the longitudinal axis direction.

The outer peripheral generating surface 56 transversely vibrates at a large amplitude of a reference amplitude V0 or more, and hence, a pressurizing and decompressing action increases in the vicinity of the outer peripheral generating surface 56. Further, the distal treatment section 42 transversely vibrates in a liquid or in a state where the liquid is present in the vicinity of the outer peripheral generating surface 56, thereby generating cavities in the liquid by the pressurizing and decompressing effect, in the vicinity of the outer peripheral generating surface 56 where the pressurizing and decompressing action caused by the transverse vibration increases. The generated cavities disappear by a force that acts in decompression of the vicinity of the outer peripheral generating surface 56. The cavities disappear, thereby generating large impact energy.

As described above, in the present embodiment, the ultrasonic vibration is transmitted to the distal treatment section 42, and hence, the cavitation phenomenon caused by the transverse vibration occurs in the outer peripheral generating surface 56 in addition to the cavitation phenomenon caused by the longitudinal vibration at the probe distal surface 45. That is, in the present embodiment, in addition to the probe distal surface 45 that is not parallel to the vibrating direction of the longitudinal vibration, the outer peripheral generating surface 56 that is not parallel to the vibrating direction of the transverse vibration is defined as the cavitation generating surface that generates the cavities in the liquid by the pressurizing and decompressing action. Additionally, the cavitation phenomenon caused by the transverse vibration does not occur at any position on the surface that is not parallel to the vibrating direction of the transverse vibration. For example, in the vicinity of the node positions N'1 and N'2 of the transverse vibration in the longitudinal axial direction, the amplitude of the transverse vibration is smaller than the reference amplitude V0. Therefore, the cavitation phenomenon caused by the transverse vibration does not occur even in the surface toward the first width direction or the second width direction, in the vicinity of the node positions N'1 and N'2 of the transverse vibration in the longitudinal axial direction.

According to the present embodiment, in the distal treatment section 42, the whole surface, other than a probe side facing surface 43 as a contact surface, and the probe distal surface 45 and the outer peripheral generating surface 56 as the cavitation generating surfaces, is coated with a coating portion 47. That is, the probe distal surface 45 in which the cavitation phenomenon caused by the longitudinal vibration occurs and the outer peripheral generating surface 56 in which the cavitation phenomenon caused by the transverse vibration occurs are not coated with the coating portion 47. Therefore, a dotted region shown in FIG. 11 is coated with the coating portion 47. Also in the present embodiment, the surface to be coated with the coating portion 47 is a finished surface 48 which is to be subjected to surface finishing so that the surface is coated with the coating portion 47 at a close contact strength of $1.33 \times 10^7$ N/m$^2$ or more.

The ultrasonic probe 31 and an ultrasonic treatment apparatus 1 of the present embodiment also have an function and an effect similar to those of the first embodiment. Additionally, in the present embodiment, the probe distal surface 45 and the outer peripheral generating surface 56 as the cavitation generating surfaces are not coated with the coating portion 47. Consequently, the peeling of the coating portion 47 due to the cavitation phenomenon caused by the longitudinal vibration is prevented, and additionally, the peeling of the coating portion 47 due to the cavitation phenomenon caused by the transverse vibration can effectively be prevented.

Modification of Second Embodiment

It is to be noted that in the second embodiment, the probe main body 41 transmits the ultrasonic vibration along the longitudinal axis C, thereby performing the transverse vibration as the vibration other than the longitudinal vibration, but it is not limited to this embodiment. For example, a distal treatment section 42 might be formed into a shape or the like suitable for a state where a probe main body 41 performs a torsional vibration as a vibration other than a longitudinal vibration. Also in a case where the probe main body 41 performs the torsional vibration, a surface that is not parallel to a vibrating direction of the vibration in the distal treatment section 42 vibrates at an amplitude of a reference amplitude V0 or more, thereby causing a cavitation phenomenon. That is, irrespective of presence or absence of occurrence of the vibration other than the longitudinal vibration and a type of vibration that occurs besides the longitudinal vibration, the surface that is not parallel to the vibrating direction in the distal treatment section 42 vibrates at the amplitude of the reference amplitude V0 or more, thereby generating cavities in a liquid by a pressurizing and decompressing action. Further, a cavitation generating surface that causes the cavitation phenomenon by the vibration of the probe main body 41 is not coated with a coating portion 47. Consequently, irrespective of the presence or absence of the occurrence of the vibration other than the longitudinal vibration and the type of vibration that occurs besides the longitudinal vibration, the peeling of the coating portion 47 due to the cavitation phenomenon can effectively be prevented.

Third Embodiment

Next, a third embodiment of the present invention will be described with reference to FIG. 13 and FIG. 14. In the third embodiment, a constitution of the first embodiment is modified as follows. It is to be noted that the same part as in the first embodiment is denoted with the same reference sign, and the description is omitted. In the present embodiment, an ultrasonic probe 31 is applied to an ultrasonic treatment instrument 61 different from a hand piece 2 that is an ultrasonic coagulation and incision treatment instrument. It is to be noted that the ultrasonic treatment instrument 61 is an ultrasonic resecting treatment instrument configured to resect a treated object such as a biological tissue by use of an ultrasonic vibration and a high frequency current.

Figure 13:
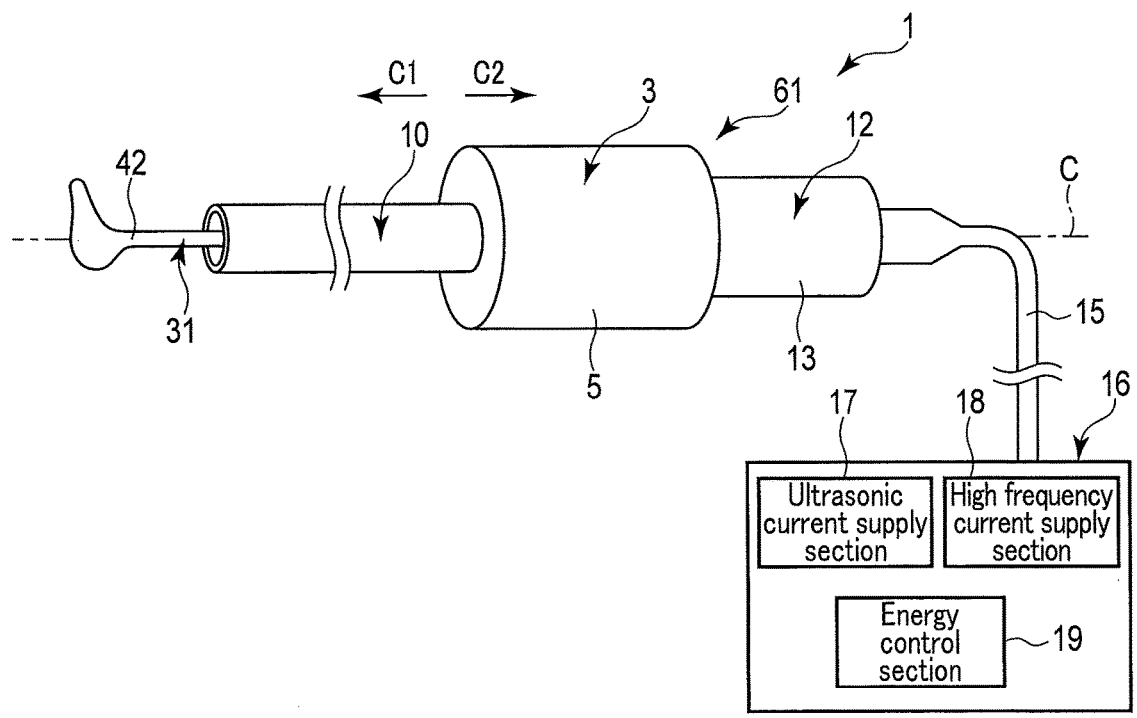
FIG. 13 is a schematic view showing a constitution of an ultrasonic treatment apparatus according to a third embodiment.

FIG. 13 is a view showing a constitution of an ultrasonic treatment apparatus 1 comprising the ultrasonic treatment instrument 61 of the present embodiment. As shown in FIG. 13, also in the ultrasonic treatment instrument 61, there are provided a holding unit 3, a transducer case 13, a sheath 10 and the ultrasonic probe 31 similarly to the hand piece 2 of the first embodiment. Further, inside the transducer case 13, an ultrasonic transducer 21 and a horn member 23 are disposed, and an ultrasonic generating current is supplied from an ultrasonic current supply section 17 of a control unit 16 to the ultrasonic vibrator 21, thereby generating an ultrasonic vibration in the ultrasonic transducer 21. Further, the ultrasonic vibration generated in the ultrasonic transducer 21 is transmitted to the ultrasonic probe 31 via the horn member 23. Additionally, a distal treatment section 42 of the ultrasonic probe 31 is provided in such a state as to project from a distal end of the sheath 10 toward a distal direction (a direction of an arrow C1 of FIG. 13). When the ultrasonic vibration transmitted to the ultrasonic probe 31 is transmitted along a longitudinal axis C in a probe main body 41, the probe main body 41 performs the abovementioned longitudinal vibration.

Additionally, in the present embodiment, a fixed handle 6, a movable handle 7 and a rotating operation knob 8 are not provided in the holding unit 3. Further, an energy operation input button (not shown in FIG. 13) that is an energy operation input portion is attached to a cylindrical case portion 5. Additionally, in the ultrasonic treatment instrument 61, a jaw 11 is not disposed. Consequently, in the present embodiment, a jaw side current path is not formed. However, also in the present embodiment, a high frequency current is supplied from a high frequency current supply section 18 to the distal treatment section 42 of the probe main body 41 through a probe side current path.

FIG. 14 is a view showing a constitution of a distal portion of the ultrasonic treatment instrument 61. As shown in FIG. 14, also in the present embodiment, a most distal antinode position A2 most distally among antinode positions of a longitudinal vibration is positioned at a distal end of the probe main body 41 (a distal end of the ultrasonic probe 31). Additionally, a most distal node position N1 most distally among node positions of the longitudinal vibration is positioned inside the sheath 10, and the distal treatment section 42 is positioned on the distal direction side with respect to the most distal node position N1 of the longitudinal vibration.

The distal treatment section 42 of the probe main body 41 includes a columnar portion 62 extended straight along the longitudinal axis C. Here, one direction perpendicular to (intersecting) the longitudinal axis C is defined as a first perpendicular direction (a direction of an arrow B3 of FIG. 14), and an opposite direction to the first perpendicular direction is defined as a second perpendicular direction (a direction of an arrow B4 of FIG. 14). In the distal treatment section 42, a hook portion 63 that is a probe curved portion is formed on the distal direction side of the columnar portion 62. In the hook portion 63, the probe main body 41 is hooked (curved) from the first perpendicular direction (a first intersecting direction) toward the second perpendicular direction (a second intersecting direction). That is, the hook portion 63 is curved relative to the longitudinal axis C in the first perpendicular direction and the second perpendicular direction. The hook portion 63 includes a curved portion surface (a hook surface) 65 that becomes the surface of the hook portion 63. The curved portion surface 65 becomes a contact surface configured to be brought into contact with a treated object such as the biological tissue in a treatment.

When an energy operation is input with the energy operation input button 9, an ultrasonic generating current is supplied from the ultrasonic current supply section 17 to the ultrasonic transducer 21 by an energy control section 19, and the high frequency current is supplied from the high frequency current supply section 18. The ultrasonic generating current is supplied to the ultrasonic transducer 21, thereby generating the ultrasonic vibration in the ultrasonic transducer 21. Further, the generated ultrasonic vibration is transmitted up to the distal treatment section 42 from a proximal direction toward the distal direction in the probe main body 41, and the probe main body 41 performs a vibration including the longitudinal vibration in a vibrating direction parallel to the longitudinal axis C. Additionally, the high frequency electric power is supplied to the distal treatment section 42 via the probe main body 41. In a state where the distal treatment section 42 to which the high frequency current is supplied is longitudinally vibrated, the curved portion surface 65 of the hook portion 63 of the distal treatment section 42 is brought into contact with a treated object such as the biological tissue, and hence, the treated object is resected.

Additionally, in the present embodiment, a probe distal surface 45 that forms the distal end of the probe main body 41 becomes a part of the curved portion surface 65. Therefore, the probe distal surface becomes a part of the contact surface to be brought into contact with the treated object.

Additionally, in the present embodiment, the hook portion 63 is provided, and hence, a gravity center G0 of the distal treatment section 42 is positioned away from the longitudinal axis C. Consequently, the probe main body 41 transmits the ultrasonic vibration along the longitudinal axis C, and hence, the probe main body 41 performs a transverse vibration in a vibrating direction parallel to the first perpendicular direction and the second perpendicular direction in addition to the longitudinal vibration. Also in the present embodiment, antinode positions A'1 and A'2 and node positions N'1 and N'2 of the transverse vibration are positioned in the distal treatment section 42 in the same manner as in the transverse vibration of the second embodiment. Further, also in the present embodiment, similarly to the second embodiment, a cavitation phenomenon caused by the transverse vibration occurs by an outer peripheral generating surface 56 directed toward the first perpendicular direction or the second perpendicular direction. That is, the outer peripheral generating surface 56 transversely vibrates at an amplitude of a reference amplitude V0 or more, thereby becoming a cavitation generating surface that generates cavities in a liquid by a pressurizing and decompressing action. Also in the present embodiment, the outer peripheral generating surface 56 is positioned in the vicinity of the antinode positions A'1 and A'2 of the transverse vibration where the amplitude of the transverse vibration increases in a longitudinal axial direction parallel to the longitudinal axis C, and the outer peripheral generating surface is positioned at a position different from the node positions N'1 and N'2 of the transverse vibration where the amplitude of the transverse vibration becomes zero in the longitudinal axial direction.

In the distal treatment section 42 of the present embodiment, the whole surface, other than the curved portion surface 65 as the contact surface (including the probe distal surface 45) and the outer peripheral generating surface 56 as the cavitation generating surface, is coated with a coating portion 47. The coating portion 47 is made of a material having a higher heat resistance than the probe main body 41 and made of an electrically insulating material in the same manner as in the first embodiment. Also in the present embodiment, similarly to the first embodiment, a PEEK, an imide modified-epoxy resin or a polyimide having a high biocompatibility is preferably used as the material of the coating portion 47.

Additionally, also in the present embodiment, a surface to be coated with the coating portion 47 in the distal treatment section 42 becomes a finished surface 48 which is subjected to surface finishing so as to heighten a surface roughness by sand blast. In the present embodiment, the surface other than the curved portion surface 65 as the distal treatment section 42 (including the probe distal surface 45) and the outer peripheral generating surface 56 becomes the finished surface 48. By the surface finishing, an oxide film is removed, and an anchoring effect is exerted between the finished surface 48 and the coating portion 47. Consequently, by the surface treating of the treated surface 48, a close contact strength of the coating portion 47 onto the finished surface 48 in the probe main body 41 heightens. Also in the present embodiment, similarly to the first embodiment, in the finished surface 48, the surface finishing is performed so that the surface is coated with the coating portion 47 at a close contact strength of $1.33 \times 10^7$ N/m$^2$ or more.

Thus, the coating portion 47 is provided, and hence, even in a case where the ultrasonic probe 31 comes in contact with the biological tissue in a region other than the treated object in the treatment, the coating portion 47 that does not reach a high temperature comes in contact with the biological tissue in the region other than the treated object. Consequently, also in the present embodiment, similarly to the first embodiment, heat damage of the biological tissue in the region other than the treated object can effectively be prevented, and a treatment performance in the treatment using the ultrasonic vibration can be secured.

Additionally, the coating portion 47 has electrically insulating properties, and hence, even in the case where the coating portion 47 comes in contact with the biological tissue in the region other than the treated object, the high frequency current is not supplied from the distal treatment section 42 to the biological tissue other than the treated object via the coating portion 47. The supply of the high frequency current from the distal treatment section 42 to the biological tissue other than the treated object is prevented, thereby heightening a current density of the high frequency current flowing through the treated object with which the curved portion surface 65 of the hook portion 63 comes in contact. In consequence, the treatment performance in the treatment using the high frequency current can improve.

Additionally, also in the present embodiment, the finished surface 48 is subjected to the surface finishing in the state where the surface is coated with the coating portion 47 at the close contact strength of $1.33 \times 10^7$ N/m$^2$ or more. Consequently, in the treatment using the ultrasonic vibration in the state where the distal treatment section 42 is positioned in the liquid where an external load due to the vibration increases, peeling of the coating portion 47 from the distal treatment section 42 can effectively be prevented.

Additionally, in the present embodiment, the outer peripheral generating surface 56 in which the cavitation phenomenon caused by the transverse vibration occurs is not coated with the coating portion 47. In consequence, the peeling of the coating portion 47 due to the cavitation phenomenon can effectively be prevented.

Modifications of Third Embodiment

It is to be noted that in the third embodiment, in the distal treatment section 42, the whole surface, other than the curved portion surface 65 as the contact surface (including the probe distal surface 45) and the outer peripheral generating surface 56 as the cavitation generating surface, is coated with the coating portion 47, but it is not limited to this embodiment. For example, as shown as a third modification that is a modification of the third embodiment in FIG. 15, in a distal treatment section 42, a part of a surface other than a curved portion surface 65 and an outer peripheral generating surface 56 in the distal treatment section 42 may be coated with a coating portion 47.

In the present modification, in the surfaces other than the curved portion surface 65 (including the probe distal surface 45) and the outer peripheral generating surface 56 in the distal treatment section, the surface faces toward a first perpendicular direction (a direction of an arrow B3 of FIG. 15) is only coated with the coating portion 47. Consequently, even in the surfaces other than the curved portion surface 65 and other than the outer peripheral generating surface 56 in the distal treatment section 42, the surface toward a second perpendicular direction (a direction of an arrow B4 of FIG. 15) that is an opposite direction to the first perpendicular direction is not coated with the coating portion 47. Also in the present modification, the surface to be coated with the coating portion 47 is a finished surface 48 which is to be subjected to surface finishing so that the surface is coated with the coating portion 47 at a close contact strength of $1.33 \times 10^7$ N/m$^2$ or more.

Additionally, in the third embodiment, the hook portion 63 is provided as a probe curved portion, but a shape of the probe curved portion is not limited to a hook shape. For example, as shown as a fourth modification that is another modification of the third embodiment in FIG. 16, a spatula portion 67 may be provided as a probe curved portion in place of the hook portion 63. The spatula portion 67 is curved relative to a longitudinal axis C in a first perpendicular direction (a direction of an arrow B3 of FIG. 16) and a second perpendicular direction (a direction of an arrow B4 of FIG. 16) in the same manner as in the hook portion 63 of the third embodiment. The spatula portion 67 includes a curved portion surface (a spatula surface) 69 that becomes the surface of the spatula portion 67, and the curved portion surface 69 becomes a contact surface to be brought into contact with a treated object such as a biological tissue in a treatment.

In the present modification, a probe distal surface 45 becomes a part of the curved portion surface 69 that is the contact surface. Additionally, in the present modification, the spatula portion 67 is provided, and hence, a gravity center G0 of a distal treatment section 42 is positioned away from a longitudinal axis C. Consequently, a probe main body 41 transmits an ultrasonic vibration along the longitudinal axis C, and hence, the probe main body 41 performs a transverse vibration in a vibrating direction parallel to the first perpendicular direction and the second perpendicular direction, in addition to a longitudinal vibration. Further, similarly to the third embodiment, a cavitation phenomenon caused by the transverse vibration occurs by an outer peripheral generating surface 56 being toward the first perpendicular direction or the second perpendicular direction.

In the present modification, in the distal treatment section 42, the whole surface, other than the curved portion surface 69 as the contact surface (including the probe distal surface 45) and the outer peripheral generating surface 56 as a cavitation generating surface, is coated with a coating portion 47. Also in the present modification, the surface to be coated with the coating portion 47 is a finished surface 48 which is to be subjected to surface finishing in a state where the surface is coated with the coating portion 47 at a close contact strength of $1.33 \times 10^7$ N/m$^2$ or more. It is to be noted that also in a case where the spatula portion 67 is provided in the distal treatment section 42, a part of the surface in the distal treatment section 42 other than the curved portion surface 69 and other than the outer peripheral generating surface 56 may be coated with the coating portion 47.

According to the abovementioned third embodiment, third modification and fourth modification, in the distal treatment section 42, at least a part of the surface other than the curved portion surface (65; 69) as the contact surface and other than the outer peripheral generating surface 56 as the cavitation generating surface may be coated with the coating portion 47. The coating portion 47 may be made of a material having a higher heat resistance than the probe main body 41. Further, the surface to be coated with the coating portion 47 may be the finished surface 48 which is to be subjected to the surface finishing in the state where the surface is coated with the coating portion 47 at the close contact strength of $1.33 \times 10^7$ N/m$^2$ or more.

Fourth Embodiment

Next, a fourth embodiment of the present invention will be described with reference to FIG. 17. In the fourth embodiment, the constitutions of the first embodiment to the third embodiment are modified as follows. It is to be noted that the same parts as in the first embodiment to the third embodiment are denoted with the same reference signs, and the descriptions are omitted.

FIG. 17 is a view showing a state where a finished surface 48 in a distal treatment section 42 is coated with a coating portion 47. The coating portion 47 is made of a material having a higher heat resistance than a probe main body 41 and having electrically insulating properties in the same manner as in the first embodiment to the third embodiment. Additionally, the finished surface 48 is subjected to surface finishing in a state where the surface is coated with the coating portion 47 at a close contact strength of $1.33 \times 10^7$ N/m$^2$ or more. The finished surface 48, to which an ultrasonic vibration is transmitted, vibrates in a vibrating direction. One side of the vibrating direction of the vibration of the finished surface 48 is defined as a first vibrating direction (a direction of an arrow T1 of FIG. 17), and an opposite direction to the first vibrating direction is defined as a second vibrating direction (a direction of an arrow T2 of FIG. 17). Here, in a case where the finished surface 48 performs a longitudinal vibration in a vibrating direction parallel to a longitudinal axis C, the first vibrating direction matches a distal direction, and the second vibrating direction matches a proximal direction. Additionally, one of directions perpendicular to the longitudinal axis C is defined as a first perpendicular direction, and an opposite direction to the first perpendicular direction is defined as a second perpendicular direction. In a case where the finished surface 48 performs a transverse vibration in a vibrating direction parallel to the first perpendicular direction and the second perpendicular direction, the first vibrating direction matches the first perpendicular direction, and the second vibrating direction matches the second perpendicular direction.

As shown in FIG. 17, the coating portion 47 has a first coating boundary P1 that is a boundary on a first vibrating direction side, and a second coating boundary P2 that is a boundary on a second vibrating direction side. The first coating boundary P1 is formed by a first coating boundary surface 71, and the second coating boundary P2 is formed by a second coating boundary surface 72. The first coating boundary surface 71 is toward the first vibrating direction, and is perpendicular to the first vibrating direction and the second vibrating direction. Additionally, the second coating boundary surface 72 is directed toward the second vibrating direction, and is perpendicular to the first vibrating direction and the second vibrating direction.

The distal treatment section 42 of the probe main body 41 includes a first abutment surface 73 on which the first coating boundary surface 71 abuts, and a second abutment surface 75 on which the second coating boundary surface 72 abuts. The first abutment surface 73 is toward the second vibrating direction, and is perpendicular to the first vibrating direction and the second vibrating direction. Additionally, the first coating boundary surface 71 does not project toward an outer direction (a direction of an arrow D1 of FIG. 17) with respect to the first abutment surface 73. As described above, the first abutment surface 73 is provided, and hence, the first coating boundary surface 71 is not exposed to the outside. Additionally, the second abutment surface 75 is directed in the first vibrating direction, and is perpendicular to the first vibrating direction and the second vibrating direction. In addition, the second coating boundary surface 72 does not project toward the outer direction with respect to the second abutment surface 75. As described above, the second abutment surface 75 is provided, and hence, the second coating boundary surface 72 is not exposed to the outside. It is to be noted that in FIG. 17, an opposite direction to the outer direction is an inner direction (a direction of an arrow D2 of FIG. 17).

In the present embodiment, the finished surface 48 which is to be coated with the coating portion 47 is disposed between the first abutment surface 73 and the second abutment surface 75 in the first vibrating direction and the second vibrating direction. The finished surface 48 is formed into a concave shape along the whole dimension between the first abutment surface 73 and the second abutment surface 75 in the first vibrating direction and the second vibrating direction. The finished surface 48 includes a first concave surface 77 extended from the first abutment surface 73 toward the second vibrating direction, and a second concave surface 78 extended from the second abutment surface 75 toward the first vibrating direction. The first concave surface 77 is formed into a dented state with the first abutment surface 73 being as a stepped portion, and the second concave surface 78 is formed in a dented state with the second abutment surface 75 being as a stepped portion. In the present embodiment, the second concave surface 78 is continuous with the second vibrating direction side of the first concave surface 77. An outer direction side of the finished surface 48 which includes the first concave surface 77 and the second concave surface 78 is coated with the coating portion 47.

Figure 18:
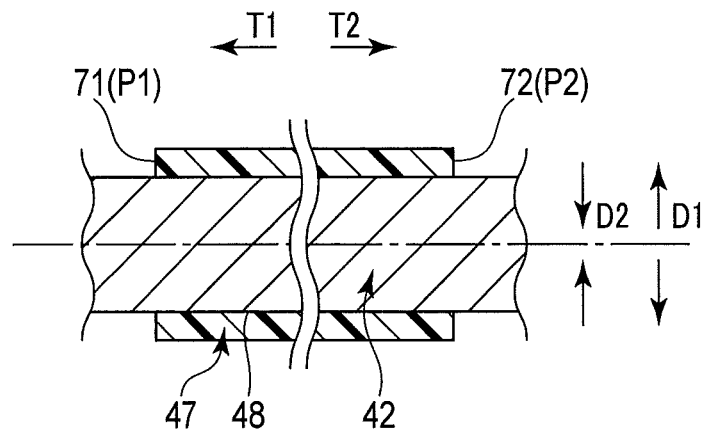
FIG. 18 is a schematic view showing a state where a finished surface in a distal treatment section according to a comparative example is coated with a coating portion.

Here, FIG. 18 shows a distal treatment section 42 and a coating portion 47 according to a comparative example. In the present comparative example, a first coating boundary surface 71 that forms a first coating boundary P1 and a second coating boundary surface 72 that forms a second coating boundary P2 are exposed to the outside. Also in the present comparative example, similarly to the fourth embodiment, the first coating boundary surface 71 faces toward a first vibrating direction (a direction of an arrow T1 of FIG. 18), and the second coating boundary surface 72 faces toward a second vibrating direction (a direction of an arrow T2 of FIG. 18). Additionally, in the present comparative example, differently from the fourth embodiment, a first abutment surface 73 and a second abutment surface 75 are not provided in the distal treatment section 42. In a case where the distal treatment section 42 (a probe main body 41) vibrates in vibrating directions that are the first vibrating direction and the second vibrating direction, an external load acts on the coating portion 47. In this case, according to the comparative example shown in FIG. 18, the external load acts in a concentrated manner on the first coating boundary surface 71 and the second coating boundary surface 72 each of which is toward one side of the vibrating direction and is exposed to the outside.

On the other hand, in the fourth embodiment, the first abutment surface 73 is provided in the distal treatment section 42, and hence, the first coating boundary surface 71 is not exposed to the outside. Consequently, in a case where the distal treatment section 42 vibrates in the first vibrating direction and the second vibrating direction, there is prevented the concentrated action of the external load onto the first coating boundary 21 formed by the first coating boundary surface 71. That is, the first coating boundary surface 71 and the first abutment surface 73 become a first load concentration preventing portion configured to prevent the concentrated action of the external load due to the vibration onto the first coating boundary P1.

Additionally, in the fourth embodiment, the second abutment surface 75 is provided in the distal treatment section 42, and hence, the second coating boundary surface 72 is not exposed to the outside. Consequently, in the case where the distal treatment section 42 vibrates in the first vibrating direction and the second vibrating direction, there is prevented the concentrated action of the external load onto the second coating boundary P2 formed by the second coating boundary surface 72. That is, the second coating boundary surface 72 and the second abutment surface 75 become a second load concentration preventing portion configured to prevent the concentrated action of the external load due to the vibration onto the second coating boundary P2. As described above, the concentrated action of the external load due to the vibration onto the first coating boundary P1 and the second coating boundary P2 is prevented, and hence, peeling of the coating portion 47 from the distal treatment section 42 can further effectively be prevented in the treatment using the ultrasonic vibration.

Modifications of Fourth Embodiment

Figure 19:
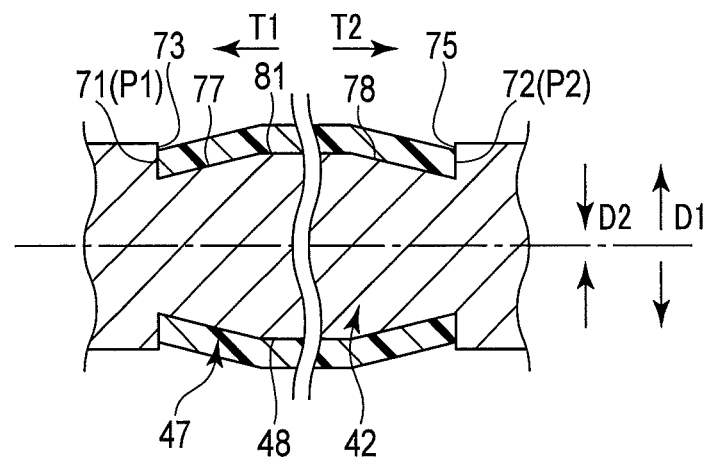
FIG. 19 is a schematic view showing a state where a finished surface in a distal treatment section according to a fifth modification is coated with a coating portion.

It is to be noted that in the fourth embodiment, the first concave surface 77 is continuous with the second concave surface 78, and the finished surface 48 is formed into the concave shape along the whole dimension between the first abutment surface 73 and the second abutment surface 75, but it is not limited to this embodiment. For example, as shown in FIG. 19 as a fifth modification that is a modification of the fourth embodiment, a finished surface 48 may include a relay surface 81 disposed between a first concave surface 77 and a second concave surface 78 in a first vibrating direction (a direction of an arrow T1 of FIG. 19) and a second vibrating direction (a direction of an arrow T2 of FIG. 19). In the present modification, the relay surface 81 is formed into a planar shape that is not concaved in an inner direction (a direction of an arrow D2 of FIG. 19). The finished surface 48 is coated with a coating portion 47 in a state where an outer direction (a direction of an arrow D1 of FIG. 19) side of the first concave surface 77, the second concave surface 78 and the relay surface 81 is coated.

Also in the present modification, similarly to the fourth embodiment, a first abutment surface 73 is provided in a distal treatment section 42, and a first coating boundary surface 71 is not exposed to the outside. Additionally, a second abutment surface 75 is disposed in the distal treatment section 42, and the second coating boundary surface 72 is not exposed to the outside. Therefore, a concentrated action of an external load due to a vibration onto a first coating boundary P1 and a second coating boundary P2 is prevented.

Figure 20:
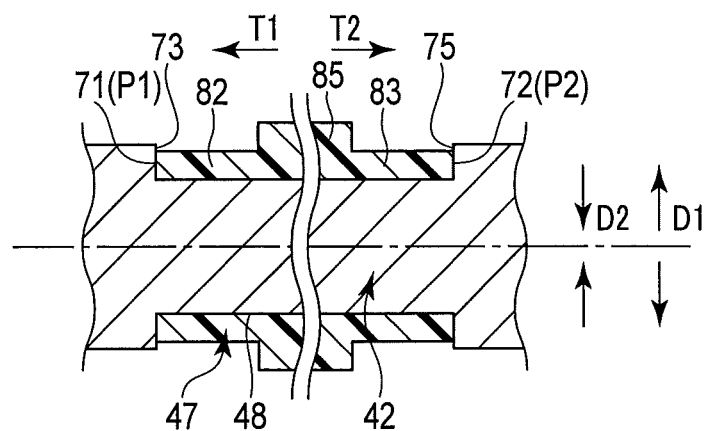
FIG. 20 is a schematic view showing a state where a finished surface in a distal treatment section according to a sixth modification is coated with a coating portion.

Additionally, in the fourth embodiment, a coating thickness of the coating portion 47 is uniform along the whole dimension in the first vibrating direction and the second vibrating direction, but it is not limited to this embodiment. For example, as shown as a sixth modification that is another modification of the fourth embodiment in FIG. 20, a coating thickness of a coating portion 47 may be non-uniform in a first vibrating direction and a second vibrating direction. In the present modification, the coating portion 47 includes a first coating thickness portion 82 extended from a first coating boundary surface 71 toward the second vibrating direction (a direction of an arrow T2 of FIG. 20), and a second coating thickness portion 83 extended from a second coating boundary surface 72 toward the first vibrating direction (a direction of an arrow T1 of FIG. 20). In the coating portion 47, a third coating thickness portion 85 is disposed between the first coating thickness portion 82 and the second coating thickness portion 83 in the first vibrating direction and the second vibrating direction. In the third coating thickness portion 85, a coating thickness is larger as compared with the first coating thickness portion 82 and the second coating thickness portion 83.

Also in the present modification, similarly to the fourth embodiment, a first abutment surface 73 is provided in a distal treatment section 42, and the first coating boundary surface 71 is not exposed to the outside. Additionally, a second abutment surface 75 is provided in the distal treatment section 42, and the second coating boundary surface 72 is not exposed to the outside. Therefore, a concentrated action of an external load due to a vibration onto a first coating boundary P1 and a second coating boundary P2 is prevented.

Figure 21:
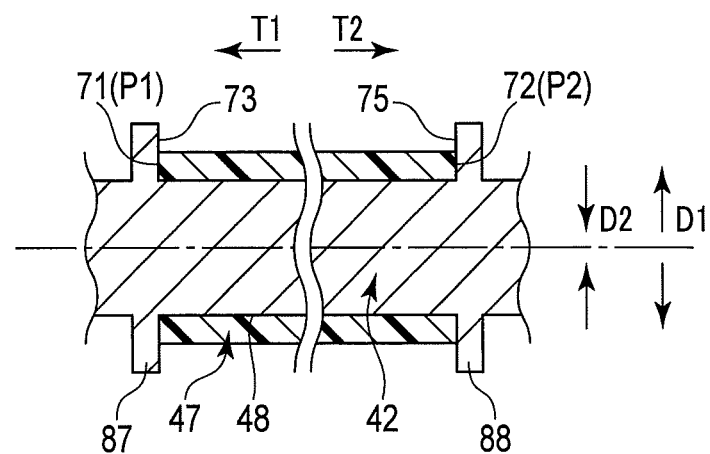
FIG. 21 is a schematic view showing a state where a finished surface in a distal treatment section according to a seventh modification is coated with a coating portion.

Additionally, as shown as a seventh modification that is still another modification of the fourth embodiment in FIG. 21, a first concave surface 77 and a second concave surface 78 do not have to be provided in a finished surface 48 which is to be coated with a coating portion 47. In the present modification, in a distal treatment section 42, there are provided a first projecting portion 87 and a second projecting portion 88 whose surfaces project toward an outer direction (a direction of an arrow D1 of FIG. 21). The second projecting portion 88 is positioned on a second vibrating direction (a direction of an arrow T2 of FIG. 21) side with respect to the first projecting portion 87. A first abutment surface 73 is formed by the first projecting portion 87, and a second abutment surface 75 is formed by the second projecting portion 88. The finished surface 48 which is to be coated with the coating portion 47 is extended between the first abutment surface 73 of the first projecting portion 87 and the second abutment surface 75 of the second projecting portion 88 in a first vibrating direction (a direction of an arrow T1 of FIG. 21) and the second vibrating direction.

Also in the present modification, similarly to the fourth embodiment, the first abutment surface 73 is provided in the distal treatment section 42, and a first coating boundary surface 71 is not exposed to the outside. Additionally, the second abutment surface 75 is provided in the distal treatment section 42, and a second coating boundary surface 72 is not exposed to the outside. Therefore, a concentrated action of an external load due to a vibration onto a first coating boundary P1 and a second coating boundary P2 is prevented.

Additionally, according to the fourth embodiment and the fifth modification to the seventh modification, the first coating boundary P1 and the second coating boundary P2 of the coating portion 47 are not exposed to the outside, but it is not limited to these examples. For example, as shown as an eighth modification that is a further modification of the fourth embodiment in FIG. 22, a first coating boundary P1 and a second coating boundary P2 may be exposed to the outside. In the present modification, in a distal treatment section 42, a first abutment surface 73 and a second abutment surface 75 are not provided.

As shown in FIG. 22, a coating portion 47 of the present modification includes a first coating thickness changing portion 91 in which a coating thickness decreases toward a first vibrating direction (a direction of an arrow T1 of FIG. 22), and a second coating thickness changing portion 92 in which a coating thickness decreases toward a second vibrating direction (a direction of an arrow T2 of FIG. 22). The first coating thickness changing portion 91 is extended up to the first coating boundary P1 toward the first vibrating direction. In the first coating boundary P1, a coating outer surface of the first coating thickness changing portion 91 forms an acute angle $\alpha 1$ relative to the second vibrating direction. The acute angle $\alpha 1$ is preferably an angle of 45° or less. The first coating thickness changing portion 91 is provided as described above, and hence, the first coating boundary P1 is formed into a shape different from a planar shape facing toward the first vibrating direction. The second coating thickness changing portion 92 is extended up to the second coating boundary P2 toward the second vibrating direction. In the second coating boundary P2, a coating outer surface of the second coating thickness changing portion 92 forms an acute angle $\alpha 2$ relative to the first vibrating direction. The acute angle $\alpha 2$ is preferably an angle of 45° or less. The second coating thickness changing portion 92 is provided as described above, and hence, the second coating boundary P2 is formed into a shape different from a planar shape directed in the second vibrating direction.

The first coating boundary P1 does not have the planar shape being toward the first vibrating direction, and hence, in a case where the distal treatment section 42 vibrates in the first vibrating direction and the second vibrating direction, a concentrated action of an external load onto the first coating boundary P1 is prevented. That is, the first coating thickness changing portion 91 becomes a first load concentration preventing portion configured to prevent the concentrated action of the external load due to the vibration onto the first coating boundary P1. The second coating boundary P2 does not have the planar shape facing toward the second vibrating direction, and hence, in a case where the distal treatment section 42 vibrates in the first vibrating direction and the second vibrating direction, the concentrated action of the external load onto the second coating boundary P2 is prevented. That is, the second coating thickness changing portion 92 becomes a second load concentration preventing portion configured to prevent the concentrated action of the external load due to the vibration onto the second coating boundary P2.

In the abovementioned fourth embodiment and the fifth modification to the eighth modification, by the first load concentration preventing portion (71, 73; 91), there is prevented the concentrated action of the external load due to the vibration onto the first coating boundary P1 that is a boundary of the coating portion 47 on the first vibrating direction side. Additionally, by the second load concentration preventing portion (72, 75; 92), there is prevented the concentrated action of the external load due to the vibration onto the second coating boundary P2 that is a boundary of the coating portion 47 on the second vibrating direction side.

Other Modifications

According to the abovementioned embodiments and modifications, in the probe main body 41, the distal treatment section 42 may be positioned on the distal direction side with respect to the most distal node position N1 positioned most distally among the node positions of the longitudinal vibration, and may treat the treated object by use of at least the ultrasonic vibration. Further, the distal treatment section 42 may include the contact surface (43; 65; 69) configured to be brought into contact with the treated object in the treatment. Further, at least a part of the surface other than the contact surface (43; 65; 69) in the distal treatment section 42 may be coated with the coating portion 47 made of the material having the higher heat resistance than the probe main body 41. Further, the finished surface 48 which is to be coated with the coating portion 47 made of a resin may be subjected to the surface finishing so that the surface is coated with the coating portion 47 at a close contact strength of $1.33 \times 10^7$ N/m$^2$ or more.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
  a high frequency supply section configured to supply a high frequency electric power;
  a probe main body extending from a proximal direction toward a distal direction along a longitudinal axis, the probe main body receiving the high frequency electric power supplied from the high frequency supply section, the probe main body being configured to transmit an ultrasonic vibration from the proximal direction toward the distal direction such that a longitudinal vibration is generated in a vibrating direction parallel to the longitudinal axis;
  a distal treatment section positioned on a distal direction side with respect to a most distal node position positioned most distally among node positions of the longitudinal vibration in the probe main body, the distal treatment section being configured to apply the ultrasonic vibration transmitted through the probe main body to a treated object, and the high frequency electric power being supplied to the distal treatment section through the probe main body such that the distal treatment section is a first electrode;
  a jaw that is openable and closable relative to the distal treatment section, the high frequency electric power being supplied to the jaw from the high frequency supply section such that the jaw is a second electrode different in potential from the first electrode in a position facing the first electrode, a high frequency current flowing between the second electrode and the first electrode when the distal treatment section is the first electrode and the jaw is the second electrode;
  a sheath through which the probe main body is inserted in a state where the distal treatment section is projected toward the distal direction, the sheath forming an electric path of the high frequency electric power that is supplied to the jaw, the sheath being spaced from the probe main body;
  a probe side facing surface provided in a position facing the jaw in a surface of the distal treatment section, the probe side facing surface being configured to grip the treated object between the probe side facing surface and the jaw, frictional heat being generated on the probe side facing surface by the longitudinal vibration of the probe main body due to the ultrasonic vibration, and the high frequency current, which flows between the first electrode and the second electrode, passing through the probe side facing surface; and
  a coating portion made of a material having electrically insulating properties and having a higher heat resistance than the probe main body, the coating portion coating the surface of the distal treatment section except for the probe side facing surface, the high frequency current that flows between the first electrode and the second electrode being prevented from passing through the coating portion due to the electrically insulating properties of the coating portion such that a current density of the high frequency current, which passes through the probe side facing surface, is increased, wherein:
  a first part that is coated with the coating portion in the surface of the distal treatment section includes a proximal-region surface located on a proximal direction side with respect to the probe side facing surface,
  the coating portion directly adheres to the surface of the distal treatment section in the proximal-region surface, and
  the proximal-region surface includes a completely-coated region, the completely-coated region being provided at least in a second part that is located inside the sheath, the coating portion coating an entire-periphery of the surface of the distal treatment section around the longitudinal axis in the completely-coated region, wherein the jaw includes a jaw inclined surface which faces the probe side facing surface and which is inclined relative to an opening and closing direction of the jaw, and a third part of the probe side facing surface which faces the jaw inclined surface is not covered with the coating portion.

2. The ultrasonic treatment apparatus of claim 1, wherein the coating portion is made of a resin, and has a close contact strength of $1.33 \times 10^7$ N/m$^2$ or more between the distal treatment section of the probe main body and the coating portion.

3. The ultrasonic treatment apparatus of claim 1, wherein the distal treatment section includes:
  a cavitation generating surface which is not parallel to the vibrating direction of the vibration, and which is configured to vibrate at an amplitude of a reference amplitude or more, thereby generating cavities in a liquid by a pressurizing and decompressing action, and
  the first part, which is coated with the coating portion in the surface of the distal treatment section, is deviated from the cavitation generating surface.

4. The ultrasonic treatment apparatus of claim 3, wherein the cavitation generating surface includes a probe distal surface which forms a distal end of the probe main body, and which is not parallel to the longitudinal axis, and
  the probe distal surface is configured to generate the cavities by the pressurizing and decompressing action caused by the longitudinal vibration.

5. The ultrasonic treatment apparatus of claim 3, wherein in a case where one direction perpendicular to the longitudinal axis is defined as a first perpendicular direction and an opposite direction to the first perpendicular direction is defined as a second perpendicular direction, the probe main body is configured to transmit the ultrasonic vibration, thereby performing a transverse vibration in a vibrating direction parallel to the first perpendicular direction and the second perpendicular direction in addition to the longitudinal vibration, and the cavitation generating surface includes an outer peripheral generating surface which faces toward the first perpendicular direction or the second perpendicular direction, and which is configured to generate the cavities by the pressurizing and decompressing action caused by the transverse vibration.

6. The ultrasonic treatment apparatus of claim 5, wherein the outer peripheral generating surface is positioned at a position different from a node position of the transverse vibration in a longitudinal axial direction parallel to the longitudinal axis.

7. The ultrasonic treatment apparatus of claim 1, further comprising:
   in a case where one of the vibrating directions of the vibration is defined as a first vibrating direction and an opposite direction to the first vibrating direction is defined as a second vibrating direction:
      a first load concentration preventing portion configured to prevent a concentrated action of an external load due to the vibration onto a first coating boundary that is a boundary of the coating portion on a first vibrating direction side; and
      a second load concentration preventing portion configured to prevent a concentrated action of the external load due to the vibration onto a second coating boundary that is a boundary of the coating portion on a second vibrating direction side.

8. The ultrasonic treatment apparatus of claim 7, wherein the first load concentration preventing portion includes:
   a first boundary surface which forms the first coating boundary, and which faces toward the first vibrating direction; and
   a first abutment surface which is provided in the distal treatment section in a state where the first abutment surface faces toward the second vibrating direction, and on which the first boundary surface abuts, the first boundary surface being formed in a state where the first boundary surface is not projected with respect to the first abutment surface toward an outer direction, and
the second load concentration preventing portion includes:
   a second boundary surface which forms the second coating boundary, and which faces toward the second vibrating direction; and
   a second abutment surface which is provided in the distal treatment section in a state where the second abutment surface faces toward the first vibrating direction, and on which the second boundary surface abuts, the second boundary surface being formed in a state where the second boundary surface is not projected with respect to the second abutment surface toward the outer direction.

9. The ultrasonic treatment apparatus of claim 8, wherein the distal treatment section includes:
   a first concave surface which is provided in the surface of the distal treatment section from the first abutment surface toward the second vibrating direction, and which is formed in a dented state with the first abutment surface being as a first stepped portion; and
   a second concave surface which is provided in the surface of the distal treatment section from the second abutment surface toward the first vibrating direction, and which is formed in a dented state with the second abutment surface being as a second stepped portion, and the surface of the distal treatment section is coated with the coating portion between the first abutment surface and the second abutment surface in a state where the coating portion covers on an outer direction side of the first concave surface and the second concave surface.

10. The ultrasonic treatment apparatus of claim 8, wherein the distal treatment section includes:
   a first projecting portion having a first surface projecting toward the outer direction, and which forms the first abutment surface; and
   a second projecting portion disposed on a second vibrating direction side with respect to the first projecting portion, and having a second surface projecting toward the outer direction, the second projecting portion forming the second abutment surface, and
the surface of the distal treatment section is coated with the coating portion between the first abutment surface of the first projecting portion and the second abutment surface of the second projecting portion.

11. The ultrasonic treatment apparatus of claim 7, wherein the first load concentration preventing portion includes a first coating thickness changing portion that extends up to the first coating boundary toward the first vibrating direction in the coating portion, and in which a coating thickness of the coating portion decreases toward the first vibrating direction, in the first coating boundary, a coating outer surface of the coating portion is extended in a state where the coating outer surface forms an acute angle relative to the second vibrating direction, and
the second load concentration preventing portion includes a second coating thickness changing portion that extends up to the second coating boundary toward the second vibrating direction in the coating portion, and in which the coating thickness of the coating portion decreases toward the second vibrating direction, in the second coating boundary, the coating outer surface is extended in a state where the coating outer surface forms an acute angle relative to the first vibrating direction.

12. The ultrasonic treatment apparatus of claim 7, wherein the first vibrating direction matches the distal direction that is one of the vibrating directions of the longitudinal vibration, and
the second vibrating direction matches the proximal direction that is the other vibrating direction of the longitudinal vibration.

13. The ultrasonic treatment apparatus of claim 1, wherein the coating portion is made of at least one of a polyether ether ketone, an imide-modified epoxy resin or a polyimide.

14. The ultrasonic treatment apparatus of claim 1, wherein the first part, which is coated with the coating portion in the surface of the distal treatment section, includes a back surface facing a side opposite to the probe side facing surface in the distal treatment section.

15. The ultrasonic treatment apparatus of claim 1, wherein the first part, which is coated with the coating portion in the surface of the distal treatment section, includes a side surface facing toward a width direction in the distal treatment section,
the width direction is transverse to the longitudinal axis and transverse to opening and closing directions of the jaw, and
the coating portion directly adheres to the surface of the distal treatment section in the side surface.

16. The ultrasonic treatment apparatus of claim 1, wherein
a shape of a cross section vertical to the longitudinal axis of the distal treatment section is polygonal, and
the portion of the polygonal closest to the jaw is not covered with the coating portion.

17. An ultrasonic treatment apparatus comprising:
a probe main body capable of transmitting ultrasonic vibration and a high-frequency current, the probe main body including a distal treatment section;
a jaw configured to open and close with respect to the probe main body, the jaw functioning as an electrode different from the probe main body, and a high-frequency current flows between the jaw and the distal treatment section of the probe main body; and
a sheath through which the probe main body is inserted in a state where the distal treatment section is projected toward the distal direction, the sheath forming an electric path of the high frequency electric power that is supplied to the jaw, the sheath being spaced from the probe main body, wherein:
the distal treatment section includes:
  a probe side facing surface that faces the jaw, the probe side facing surface being configured to grip a treated object between the probe side facing surface and the jaw,
  a back surface disposed opposite to the probe side facing surface, and
  a proximal-region surface located on a proximal direction side with respect to the probe side facing surface;
the back surface and the proximal-region surface are coated with an electrically insulating material, and a distal end of the probe main body and the probe side facing surface are not coated with the electrically insulating material; and
the proximal-region surface includes a completely-coated region, the completely-coated region being provided at least in a part that is located inside the sheath, the completely-coated region being coated with the electrically insulating material in an entire-periphery of the distal treatment section around the longitudinal axis, wherein an inclination angle of the jaw inclined surface is aligned with an inclination angle of the probe side facing surface.

18. The ultrasonic treatment apparatus of claim 1, wherein the completely-coated region continuously extends up to the most distal node toward the proximal direction.

19. The ultrasonic treatment apparatus of claim 1, wherein
the distal treatment section includes a taper portion located on the proximal direction side with respect to the probe side facing surface, a sectional area of the distal treatment section perpendicular to the longitudinal axis decreasing from the proximal direction toward the distal direction in the taper portion, and
the completely-coated region is located in the taper portion.

20. The ultrasonic treatment apparatus of claim 1, wherein
the jaw includes a member in a central portion with respect to a width direction of the jaw, and
the member projects toward the probe main body and the probe side facing surface, where the probe side facing surface is not covered with the coating portion.

21. The ultrasonic treatment apparatus of claim 1, wherein
the jaw is configured to pivot about a pivot axis relative to the sheath thereby being openable and closable relative to the distal treatment section, and
the pivot axis of the jaw is located in a partially-covering part of the sheath.

22. The ultrasonic treatment apparatus of claim 1, wherein
a distal end of the sheath is located on the proximal direction side with respect to the probe side facing surface, and
the completely-coated region is located on the proximal direction side with respect to the distal end of the sheath.

* * * * *